(12) United States Patent
Knowles et al.

(10) Patent No.: US 7,279,232 B2
(45) Date of Patent: Oct. 9, 2007

(54) ELECTROLUMINESCENT STABILITY

(75) Inventors: David B. Knowles, Apollo, PA (US); Raymond Kwong, Plainsboro, NJ (US)

(73) Assignee: Universal Display Corporation, Ewing, NJ (US)

( * ) Notice: Subject to any disclaimer, the term of this patent is extended or adjusted under 35 U.S.C. 154(b) by 248 days.

(21) Appl. No.: 10/765,295

(22) Filed: Jan. 26, 2004

(65) Prior Publication Data

US 2005/0164030 A1    Jul. 28, 2005

(51) Int. Cl.
H01L 51/54 (2006.01)
C09K 11/06 (2006.01)

(52) U.S. Cl. .............. 428/690; 428/917; 313/504; 546/4; 546/10; 257/E51.044

(58) Field of Classification Search ............ None
See application file for complete search history.

(56) References Cited

U.S. PATENT DOCUMENTS

| | | | | |
|---|---|---|---|---|
| 4,769,292 | A | 9/1988 | Tang et al. | 428/690 |
| 5,247,190 | A | 9/1993 | Friend et al. | 257/40 |
| 5,703,436 | A | 12/1997 | Forrest et al. | 313/506 |
| 5,707,745 | A | 1/1998 | Forrest et al. | 428/432 |
| 5,834,893 | A | 11/1998 | Bulovic et al. | 313/506 |
| 5,844,363 | A | 12/1998 | Gu et al. | 313/506 |
| 6,013,982 | A | 1/2000 | Thompson et al. | 313/506 |
| 6,087,196 | A | 7/2000 | Sturm et al. | 438/29 |
| 6,091,195 | A | 7/2000 | Forrest et al. | 313/504 |
| 6,097,147 | A | 8/2000 | Baldo et al. | 313/506 |
| 6,294,398 | B1 | 9/2001 | Kim et al. | 438/22 |
| 6,303,238 | B1 | 10/2001 | Thompson et al. | 428/690 |
| 6,337,102 | B1 | 1/2002 | Forrest et al. | 427/64 |
| 6,468,819 | B1 | 10/2002 | Kim et al. | 438/22 |
| 2003/0054198 | A1 | 3/2003 | Tsuboyama et al. | 428/690 |
| 2003/0059646 | A1* | 3/2003 | Kamatani et al. | 428/690 |
| 2003/0230980 | A1 | 12/2003 | Forrest et al. | 313/600 |
| 2003/0235712 | A1* | 12/2003 | Takiguchi et al. | 428/690 |
| 2004/0086743 | A1* | 5/2004 | Brown et al. | 428/690 |
| 2004/0174116 | A1 | 9/2004 | Lu et al. | 313/506 |

FOREIGN PATENT DOCUMENTS

| | | |
|---|---|---|
| EP | 1 239 526 | 9/2002 |
| EP | 1 348 711 | 10/2003 |
| GB | 2 404 380 | 2/2005 |
| JP | 2004-319438 | 11/2004 |
| WO | WO 02/15645 A1 | 2/2002 |
| WO | 02/081488 | 10/2002 |
| WO | WO 03/000661 A1 * | 1/2003 |
| WO | 03/084973 | 10/2003 |

OTHER PUBLICATIONS

Baldo et al., "Highly Efficient Phosphorescent Emission from Organic Electroluminescent Devices," Nature, vol. 395, 151-154 (1998).

Baldo et al., "Very high-efficiency green organic light-emitting devices based on electropohosphorescence," Applied Physics Letters, vol. 75, No. 1, (1999).

Adachi et al., Nearly 100% Internal Phosphorescent Efficiency in an Organic Light Emitting Device, J. Appl. Phys., 90, 5048-5051 (2001).

Kwong et al., << High operational stability of electrophosphorescent devices >>, Appl. Phys. Lett., 81, pp. 162-164 (2002).

International Search Report, Appln. No. PCT/US2005/001720, filed Jan. 19, 2005.

Patent Abstracts of Japan, vol. 2003, No. 12, Dec. 5, 2003 & JP 2004 319438, 2003 ?.

Tsuzuki et al., "Color Tunable Organic Light-Emitting Diodes Using Pentafluorophenyl-Substituted Iridium Complexes", Adv. Materials, vol. 15, No. 17, p. 1455-1458, 2003.

* cited by examiner

Primary Examiner—Marie Yamnitzky
(74) Attorney, Agent, or Firm—Kenyon & Kenyon LLP

(57) ABSTRACT

An organic light emitting device is provided. The device has an anode, a cathode, and an emissive layer disposed between the anode and the cathode. The emissive layer further comprises an emissive material having the structure:

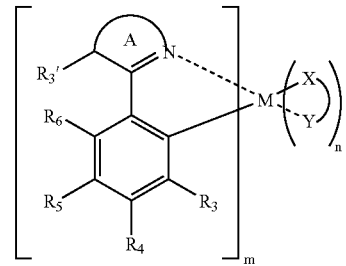

wherein M is a metal having an atomic weight greater than 40;

ring A is an aromatic heterocyclic or a fused aromatic heterocyclic ring with at least one nitrogen atom that is coordinated to the metal M, wherein the ring A can be optionally substituted;

(X—Y) is an ancillary ligand;

m is a value from 1 to the maximum number of ligands that may be attached to the metal; and m+n is the maximum number of ligands that may be attached to the metal.

The emissive material itself is also provided. The emissive material may have improved efficiency and stability when incorporated into a light emitting device.

50 Claims, 18 Drawing Sheets

ELECTROLUMINESCENT STABILITY

The claimed invention was made by, on behalf of, and/or in connection with one or more of the following parties to a joint university corporation research agreement: Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs), and more specifically to phosphorescent organic materials used in such devices. More specifically, the present invention relates to phosphorescent emitting materials with improved electroluminescent stability when incorporated into an OLED.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

OLED devices are generally (but not always) intended to emit light through at least one of the electrodes, and one or more transparent electrodes may be useful in an organic opto-electronic devices. For example, a transparent electrode material, such as indium tin oxide (ITO), may be used as the bottom electrode. A transparent top electrode, such as disclosed in U.S. Pat. Nos. 5,703,436 and 5,707,745, which are incorporated by reference in their entireties, may also be used. For a device intended to emit light only through the bottom electrode, the top electrode does not need to be transparent, and may be comprised of a thick and reflective metal layer having a high electrical conductivity. Similarly, for a device intended to emit light only through the top electrode, the bottom electrode may be opaque and/or reflective. Where an electrode does not need to be transparent, using a thicker layer may provide better conductivity, and using a reflective electrode may increase the amount of light emitted through the other electrode, by reflecting light back towards the transparent electrode. Fully transparent devices may also be fabricated, where both electrodes are transparent. Side emitting OLEDs may also be fabricated, and one or both electrodes may be opaque or reflective in such devices.

As used herein, "top" means furthest away from the substrate, while "bottom" means closest to the substrate. For example, for a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

Industry standards call for the lifetime of such full color displays to be at least about 5000 hours. In addition, high stability and efficiency are important characteristics of high quality displays. These requirements have helped generate a need for phosphorescent emissive materials that exhibit longer lifetimes, higher stability, and higher efficiency in the red, green and blue wavelength regimes than have been achieved in the prior art.

One example of a green emissive molecule is tris(2-phenylpyridine) iridium, denoted Ir(ppy)$_3$, which has the structure of Formula I:

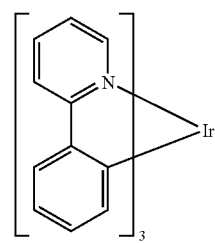

In this, and later figures herein, we depict the dative bond from nitrogen to metal (here, Ir) as a straight line. Ir(ppy)$_3$ emits a spectrum at CIE 0.30, 0.63, and has a halflife of

SUMMARY OF THE INVENTION

An organic light emitting device is provided. The device has an anode, a cathode, and an emissive layer disposed between the anode and the cathode. The emissive layer further comprises an emissive material having the structure:

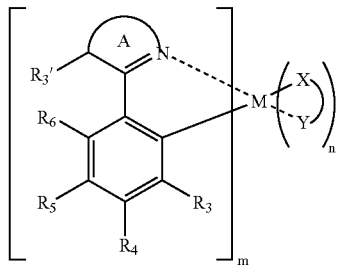

wherein M is a metal having an atomic weight greater than 40;

$R_3'$ is a substituent selected from the group consisting of alkyl, heteroalkyl, aryl, heteroaryl, and aralkyl, wherein $R_3'$ is optionally substituted by one or more substituents Z;

$R_5$ is a substituent selected from the group consisting of aryl and heteroaryl, wherein said aryl or heteroaryl is unsubstituted or optionally, substituted with one or more non-aromatic groups;

ring A is an aromatic heterocyclic or a fused aromatic heterocyclic ring with at least one nitrogen atom that is coordinated to the metal M, wherein the ring A can be optionally substituted with one or more substituents Z;

$R_3$ is a substituent selected from the group consisting of H, alkyl, alkenyl, alkynyl, alkylaryl, CN, $CF_3$, $C_nF_{2n+1}$, trifluorovinyl, $CO_2R$, $C(O)R$, $NR_2$, $NO_2$, OR, halo, aryl, heteroaryl, substituted aryl, substituted heteroaryl or a heterocyclic group;

$R_4$ is a substitutent selected from the group consisting of H, alkyl, alkenyl, alkynyl, alkylaryl, CN, $CF_3$, $C_nF_{2n+1}$, trifluorovinyl, $CO_2R$, $C(O)R$, $NR_2$, $NO_2$, OR, halo, aryl, heteroaryl, substituted aryl, substituted heteroaryl or a heterocyclic group;

additionally or alternatively, $R_3$ and $R_4$, together from independently a fused 4 to 7-member cyclic group, wherein said cyclic group is cycloalkyl, cycloheteroalkyl, aryl, or heteroaryl; and wherein said cyclic group is optionally substituted by one or more substitutents Z;

$R_6$ is a substitutent selected from the group consisting of H, alkyl, alkenyl, alkynyl, alkylaryl, CN, $CF_3$, $C_nF_{2n+1}$, trifluorovinyl, $CO_2R$, $C(O)R$, $NR_2$, $NO_2$, OR, halo, aryl, heteroaryl, substituted aryl, substituted heteroaryl or a heterocyclic group;

alternatively, $R_3'$ and $R_6$ may be bridged by a group selected from —$CR_2$—$CR_2$—, —CR=CR—, —$CR_2$—, —O—, —NR—, —O—$CR_2$—, —NR—$CR_2$—, and —N=CR—;

each R is independently H, alkyl, alkenyl, alkynyl, heteroalkyl, aryl, heteroaryl, or aralkyl; wherein R is optionally substituted by one or more substituents Z;

each Z is independently a halogen, R', O—R', $N(R')_2$, SR', C(O)R', C(O)OR', $C(O)N(R')_2$, CN, $NO_2$, $SO_2$, SOR', $SO_2R'$, or $SO_3R'$;

Each R' is independently H, alkyl, perhaloalkyl, alkenyl, alkynyl, heteroalkyl, aryl, or heteroaryl;

(X—Y) is an ancillary ligand;

m is a value from 1 to the maximum number of ligands that may be attached to the metal;

and m+n is the maximum number of ligands that may be attached to the metal.

The emissive material itself is also provided. The emissive material may have improved efficiency and stability when incorporated into a light emitting device. Additionally, the devices of the present invention are expected to exhibit improved quantum efficiency.

DETAILED DESCRIPTION

Figure 1:
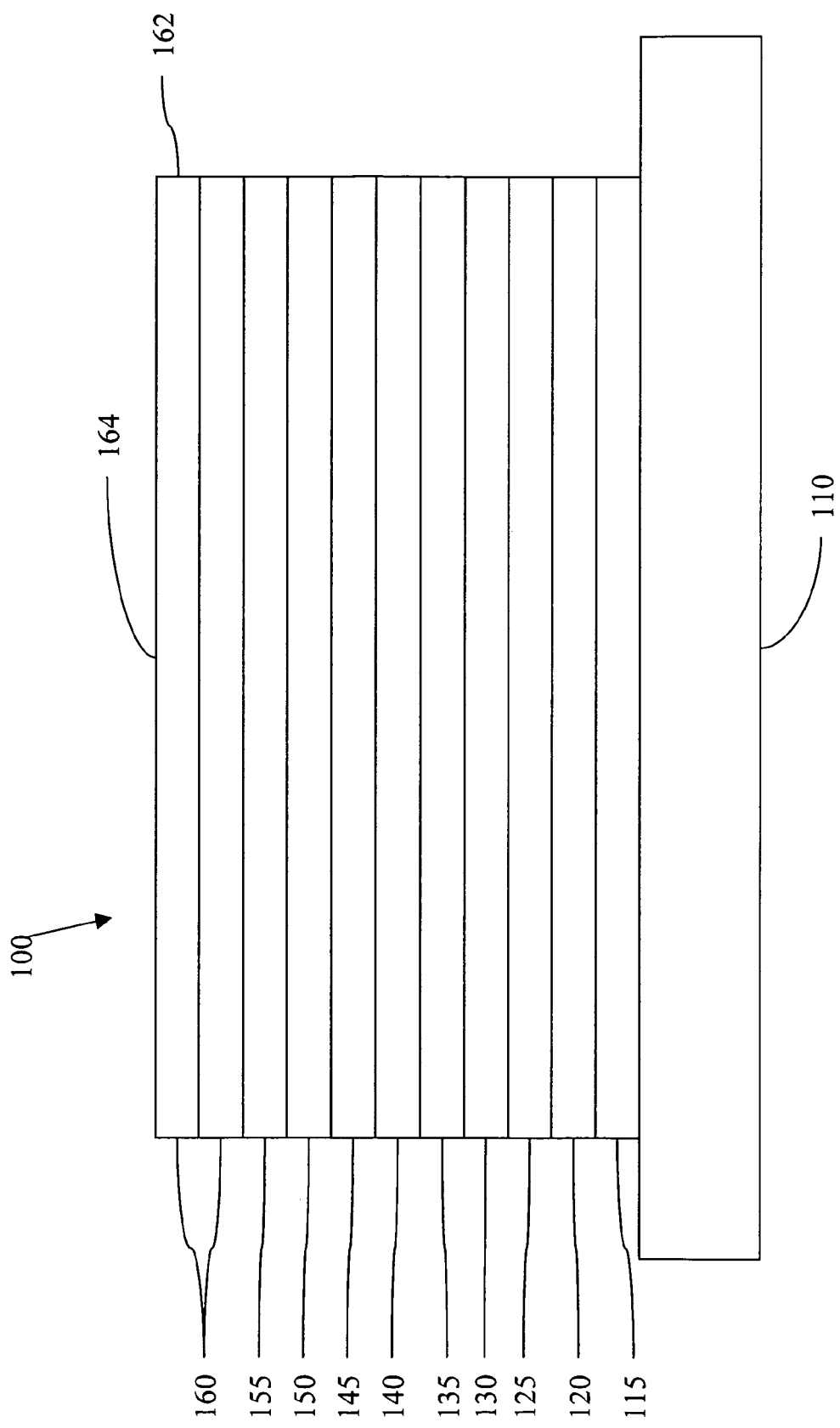
FIG. 1 shows an organic light emitting device having separate electron transport, hole transport, and emissive layers, as well as other layers.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a non-radiative mechanism, such that no light is emitted. Organic phosphorescence is also often observed in molecules containing heteroatoms with unshared pairs of electrons at very low temperatures. 2,2'-bipyridine is such a molecule. Non-radiative decay mechanisms are typically temperature dependent, such that a material that exhibits phosphorescence at liquid nitrogen temperatures may not exhibit phosphorescence at room temperature. But, as demonstrated by Baldo, this problem may be addressed by selecting phosphorescent compounds that do phosphoresce at room temperature.

Generally, the excitons in an OLED are believed to be created in a ratio of about 3:1, i.e., approximately 75% triplets and 25% singlets. See, Adachi et al., "Nearly 100% Internal Phosphorescent Efficiency In An Organic Light Emitting Device," J. Appl. Phys., 90, 5048 (2001), which is incorporated by reference in its entirety. In many cases, singlet excitons may readily transfer their energy to triplet excited states via "intersystem crossing," whereas triplet excitons may not readily transfer their energy to singlet excited states. As a result, 100% internal quantum efficiency is theoretically possible with phosphorescent OLEDs. In a fluorescent device, the energy of triplet excitons is generally lost to radiationless decay processes that heat-up the device, resulting in much lower internal quantum efficiencies. OLEDs utilizing phosphorescent materials that emit from triplet excited states are disclosed, for example, in U.S. Pat. No. 6,303,238, which is incorporated by reference in its entirety.

Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

Phosphorescence from triplets can be enhanced over fluorescence by confining, preferably through bonding, the organic molecule in close proximity to an atom of high atomic number. This phenomenon, called the heavy atom effect, is created by a mechanism known as spin-orbit coupling. Such a phosphorescent transition may be observed from an excited metal-to-ligand charge transfer (MLCT) state of an organometallic molecule such as tris(2-phenylpyridine)iridium(III).

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order.

Substrate 110 may be any suitable substrate that provides desired structural properties. Substrate 110 may be flexible or rigid. Substrate 110 may be transparent, translucent or opaque. Plastic and glass are examples of preferred rigid substrate materials. Plastic and metal foils are examples of preferred flexible substrate materials. Substrate 110 may be a semiconductor material in order to facilitate the fabrication of circuitry. For example, substrate 110 may be a silicon wafer upon which circuits are fabricated, capable of controlling OLEDs subsequently deposited on the substrate. Other substrates may be used. The material and thickness of substrate 110 may be chosen to obtain desired structural and optical properties.

Anode 115 may be any suitable anode that is sufficiently conductive to transport holes to the organic layers. The material of anode 115 preferably has a work function higher than about 4 eV (a "high work function material"). Preferred anode materials include conductive metal oxides, such as indium tin oxide (ITO) and indium zinc oxide (IZO), aluminum zinc oxide (AlZnO), and metals. Anode 115 (and substrate 110) may be sufficiently transparent to create a bottom-emitting device. A preferred transparent substrate and anode combination is commercially available ITO (anode) deposited on glass or plastic (substrate). A flexible and transparent substrate-anode combination is disclosed in U.S. Pat. No. 5,844,363, which is incorporated by reference in its entirety. Anode 115 may be opaque and/or reflective. A reflective anode 115 may be preferred for some top-emitting devices, to increase the amount of light emitted from the top of the device. The material and thickness of anode 115 may be chosen to obtain desired conductive and optical properties. Where anode 115 is transparent, there may be a range of thickness for a particular material that is thick enough to provide the desired conductivity, yet thin enough to provide the desired degree of transparency. Other anode materials and structures may be used.

Hole transport layer 125 may include a material capable of transporting holes. Hole transport layer 130 may be intrinsic (undoped), or doped. Doping may be used to enhance conductivity. α-NPD and TPD are examples of intrinsic hole transport layers. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Other hole transport layers may be used.

Emissive layer 135 may include an organic material capable of emitting light when a current is passed between anode 115 and cathode 160. Preferably, emissive layer 135 contains a phosphorescent emissive material, although fluorescent emissive materials may also be used. Phosphorescent materials are preferred because of the higher luminescent efficiencies associated with such materials. Emissive layer 135 may also comprise a host material capable of transporting electrons and/or holes, doped with an emissive material that may trap electrons, holes, and/or excitons, such that excitons relax from the emissive material via a photoemissive mechanism. Emissive layer 135 may comprise a single material that combines transport and emissive properties. Whether the emissive material is a dopant or a major constituent, emissive layer 135 may comprise other materials, such as dopants that tune the emission of the emissive material. Emissive layer 135 may include a plurality of emissive materials capable of, in combination, emitting a desired spectrum of light. Examples of phosphorescent emissive materials include Ir(ppy)$_3$. Examples of fluorescent emissive materials include DCM and DMQA. Examples of host materials include Alq$_3$, CBP and mCP. Examples of emissive and host materials are disclosed in U.S. Pat. No. 6,303,238 to Thompson et al., which is incorporated by reference in its entirety. Emissive material may be included in emissive layer 135 in a number of ways. For example, an emissive small molecule may be incorporated into a polymer. Other emissive layer materials and structures may be used.

Electron transport layer 140 may include a material capable of transporting electrons. Electron transport layer 140 may be intrinsic (undoped), or doped. Doping may be used to enhance conductivity. Alq$_3$ is an example of an intrinsic electron transport layer. An example of an n-doped electron transport layer is BPhen doped with Li at a molar ratio of 1:1, as disclosed in U.S. Patent Application Publication No. 2003/0230980, which is incorporated by reference in its entirety. Other electron transport layers may be used.

The charge carrying component of the electron transport layer may be selected such that electrons can be efficiently injected from the cathode into the LUMO (Lowest Unoccupied Molecular Orbital) level of the electron transport layer. The "charge carrying component" is the material responsible for the LUMO that actually transports electrons. This component may be the base material, or it may be a dopant. The LUMO level of an organic material may be generally characterized by the electron affinity of that material and the relative electron injection efficiently of a cathode may be generally characterized in terms of the work function of the cathode material. This means that the preferred properties of an electron transport layer and the adjacent cathode may be specified in terms of the electron affinity of the charge carrying component of the ETL and the work function of the cathode material. In particular, so as to achieve high electron injection efficiency, the work function of the cathode material is preferably not greater than the electron affinity of the charge carrying component of the electron transport layer by more than about 0.75 eV, more preferably, by not more than about 0.5 eV. Similar considerations apply to any layer into which electrons are being injected.

Cathode 160 may be any suitable material or combination of materials known to the art, such that cathode 160 is capable of conducting electrons and injecting them into the organic layers of device 100. Cathode 160 may be transparent or opaque, and may be reflective. Metals and metal oxides are examples of suitable cathode materials. Cathode 160 may be a single layer, or may have a compound structure. FIG. 1 shows a compound cathode 160 having a thin metal layer 162 and a thicker conductive metal oxide layer 164. In a compound cathode, preferred materials for the thicker layer 164 include ITO, IZO, and other materials known to the art. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The part of cathode 160 that is in contact with the underlying organic layer, whether it is a single layer cathode 160, the thin metal layer 162 of a compound cathode, or some other part, is preferably made of a material having a work function lower than about 4 eV (a "low work function material"). Other cathode materials and structures may be used.

Blocking layers may be used to reduce the number of charge carriers (electrons or holes) and/or excitons that leave the emissive layer. An electron blocking layer 130 may be disposed between emissive layer 135 and the hole transport layer 125, to block electrons from leaving emissive layer 135 in the direction of hole transport layer 125. Similarly, a hole blocking layer 140 may be disposed between emissive layer 135 and electron transport layer 145, to block holes from leaving emissive layer 135 in the direction of electron transport layer 140. Blocking layers may also be used to block excitons from diffusing out of the emissive layer. The theory and use of blocking layers is described in more detail in U.S. Pat. No. 6,097,147 and U.S. Patent Application Publication No. 2003/0230980, which are incorporated by reference in their entireties.

As would be generally understood by one skilled in the art, use of the term "blocking" layer is meant to suggest that the layer is comprised of a material, or materials, that provide a barrier that significantly inhibits transport of charge carriers and/or excitons through the layer, without suggesting or implying that the barrier completely blocks all charge carriers and/or excitons. The presence of such a barrier typically manifests itself in terms of producing substantially higher efficiencies as compared to devices lacking the blocking layer, and/or in terms of confining the emission to the desired region of the OLED.

Generally, injection layers are comprised of a material that may improve the injection of charge carriers from one layer, such as an electrode or an organic layer, into an adjacent organic layer. Injection layers may also perform a charge transport function. In device 100, hole injection layer 120 may be any layer that improves the injection of holes from anode 115 into hole transport layer 125. CuPc is an example of a material that may be used as a hole injection layer from an ITO anode 115, and other anodes. In device 100, electron injection layer 150 may be any layer that improves the injection of electrons into electron transport layer 145. LiF/Al is an example of a material that may be used as an electron injection layer into an electron transport layer from an adjacent layer. Other materials or combinations of materials may be used for injection layers. Depending upon the configuration of a particular device, injection layers may be disposed at locations different than those shown in device 100. More examples of injection layers are provided in U.S. Patent Application Publication No. 2004/0174116, which is incorporated by reference in its entirety. A hole injection layer may comprise a solution deposited material, such as a spin-coated polymer, e.g., PEDOT:PSS, or it may be a vapor deposited small molecule material, e.g., CuPc or MTDATA.

A hole injection layer (HIL) may planarize or wet the anode surface so as to provide efficient hole injection from the anode into the hole injecting material. A hole injection layer may also have a charge carrying component having HOMO (Highest Occupied Molecular Orbital) energy levels that favorably match up, as defined by their herein-described relative ionization potential (IP) energies, with the adjacent anode layer on one side of the HIL and the hole transporting layer on the opposite side of the HIL. In this case, the "charge carrying component" is the material responsible for the HOMO that actually transports holes. This component may be the base material of the HIL, or it may be a dopant. Using a doped HIL allows the dopant to be selected for its electrical properties, and the host to be selected for morphological properties such as wetting, flexibility, toughness, etc. Preferred properties for the HIL material are such that holes can be efficiently injected from the anode into the HIL material. In particular, the charge carrying component of the HIL preferably has an IP not more than about 0.7 eV greater that the IP of the anode material. More preferably, the charge carrying component has an IP not more than about 0.5 eV greater than the anode material. Similar considerations apply to any layer into which holes are being injected. HIL materials may be further distinguished from conventional hole transporting materials that are typically used in the hole transporting layer of an OLED in that such HIL materials may have a hole conductivity that is substantially less than the hole conductivity of conventional hole transporting materials. The thickness of the HIL may be thick enough to help planarize or wet the surface of the anode layer. For example, an HIL thickness of as little as 10 nm may be acceptable for a very smooth anode surface. However, since anode surfaces tend to be very rough, a thickness for the HIL of up to 50 nm may be desired in some cases.

A protective layer may be used to protect underlying layers during subsequent fabrication processes. For example, the processes used to fabricate metal or metal oxide top electrodes may damage organic layers, and a protective layer may be used to reduce or eliminate such damage. In device 100, protective layer 155 may reduce damage to underlying organic layers during the fabrication of cathode 160. Preferably, a protective layer has a high carrier mobility for the type of carrier that it transports (electrons in device 100), such that it does not significantly increase the operating voltage of device 100. CuPc, BCP, and various metal phthalocyanines are examples of materials that may be used in protective layers. Other materials or combinations of materials may be used. The thickness of protective layer 155 is preferably thick enough that there is little or no damage to underlying layers due to fabrication processes that occur after organic protective layer 160 is deposited, yet not so thick as to significantly increase the operating voltage of device 100. Protective layer 155 may be doped to increase its conductivity. For example, a CuPc or BCP protective layer 160 may be doped with Li. A more detailed description of protective layers may be found in U.S. Patent Application Publication No. 2004/0174116, which is incorporated by reference in its entirety.

Figure 2:
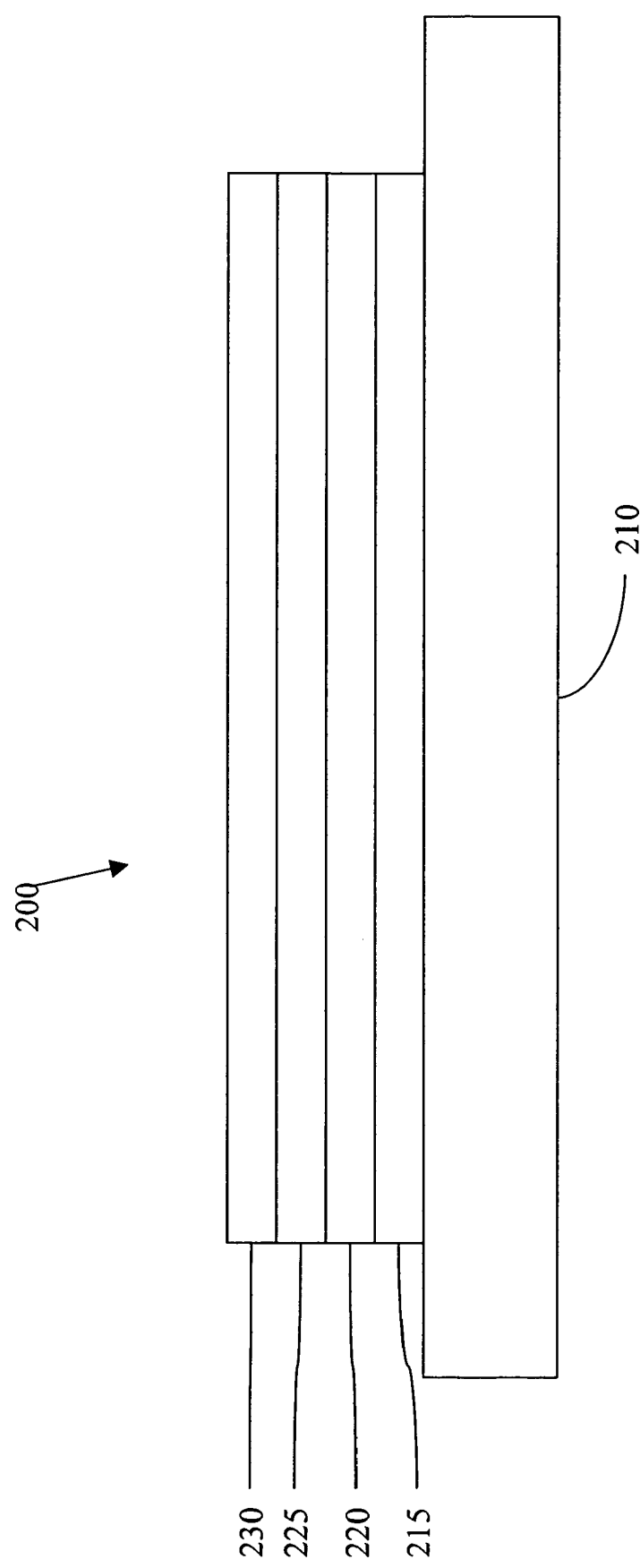
FIG. 2 shows an inverted organic light emitting device that does not have a separate electron transport layer.
Figure 3:
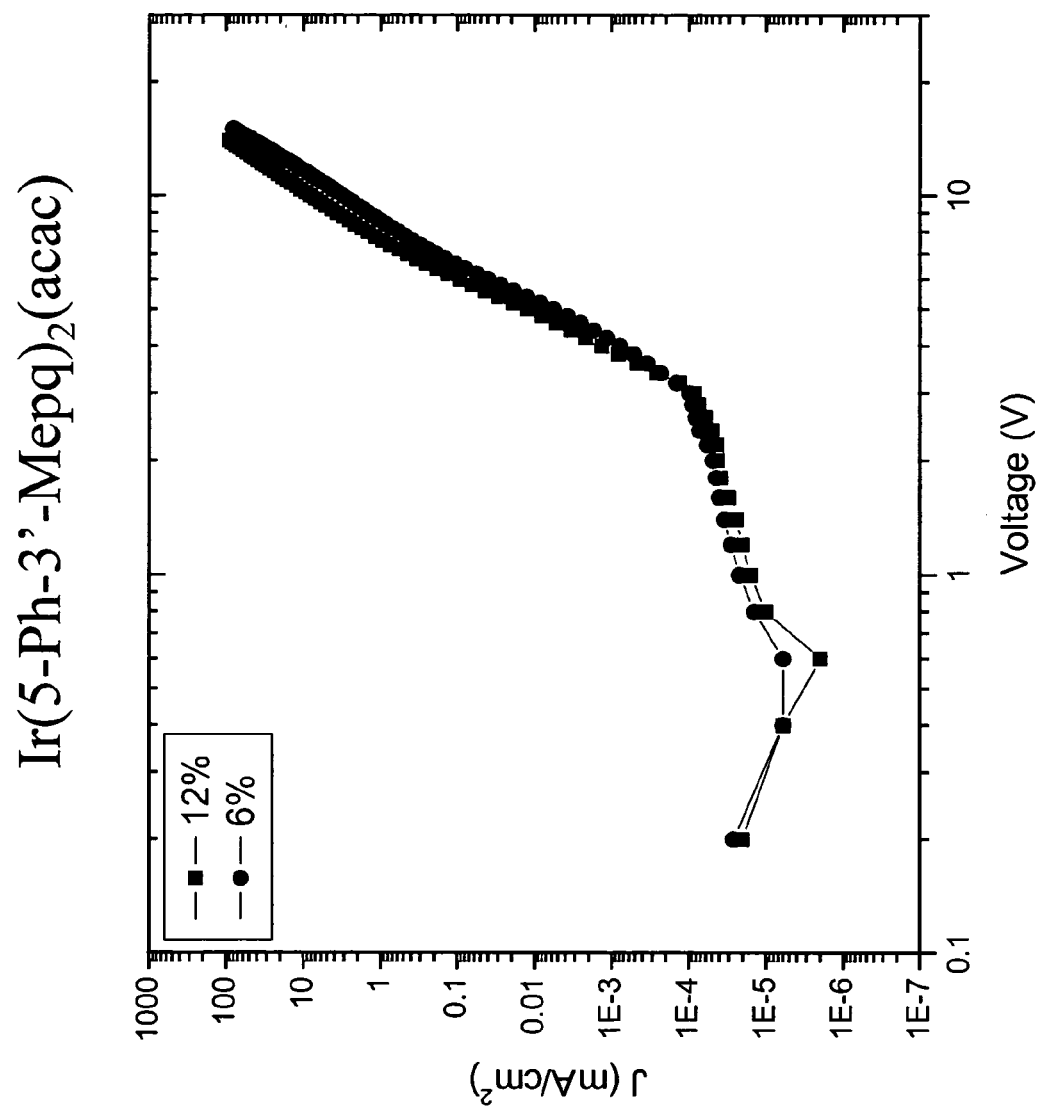
FIG. 3 shows plots of current density vs. voltage for a Ir(5-Ph-3'-Mepq)$_2$(acac) device at dopant concentrations of 6% and 12% in a log scale (all dopant concentrations are in wt % unless otherwise specified).
Figure 4:
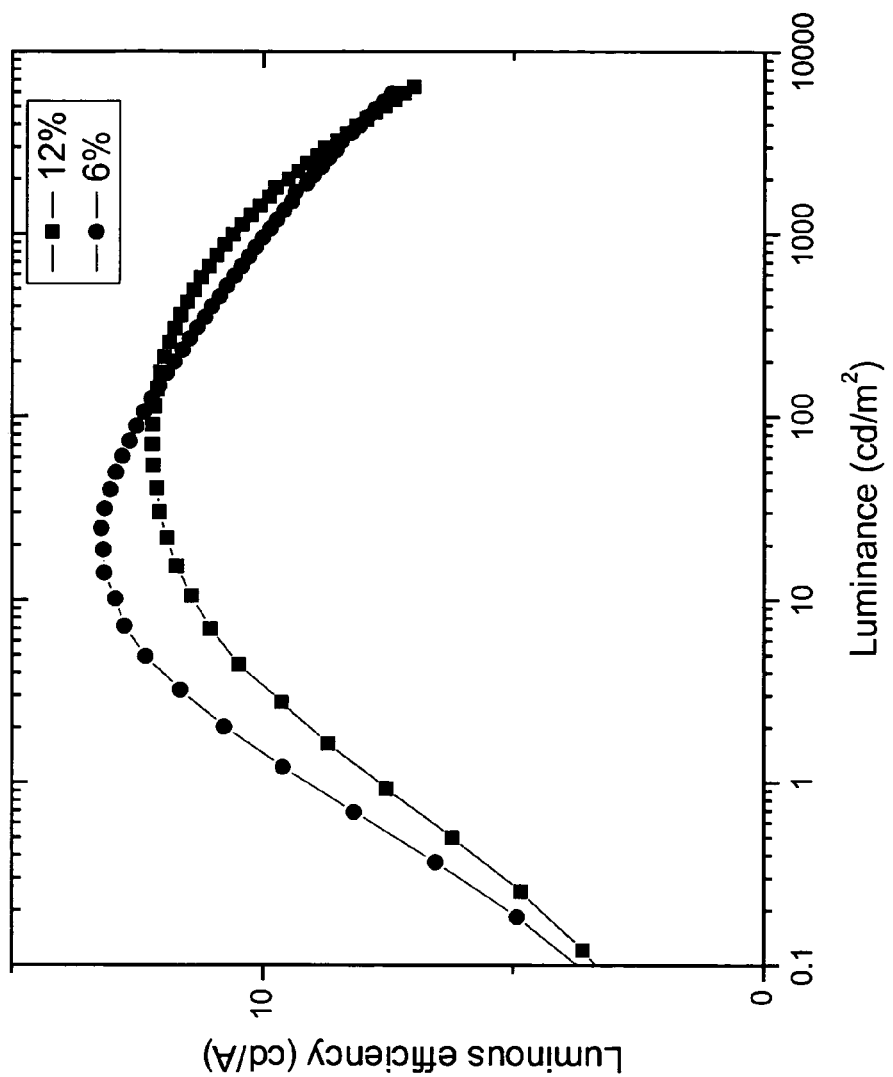
FIG. 4 shows plots of luminous efficiency (cd/A) vs. brightness (cd/m$^2$) voltage for a Ir(5-Ph-3'-Mepq)$_2$(acac) device at dopant concentrations of 6% and 12%.
Figure 5:
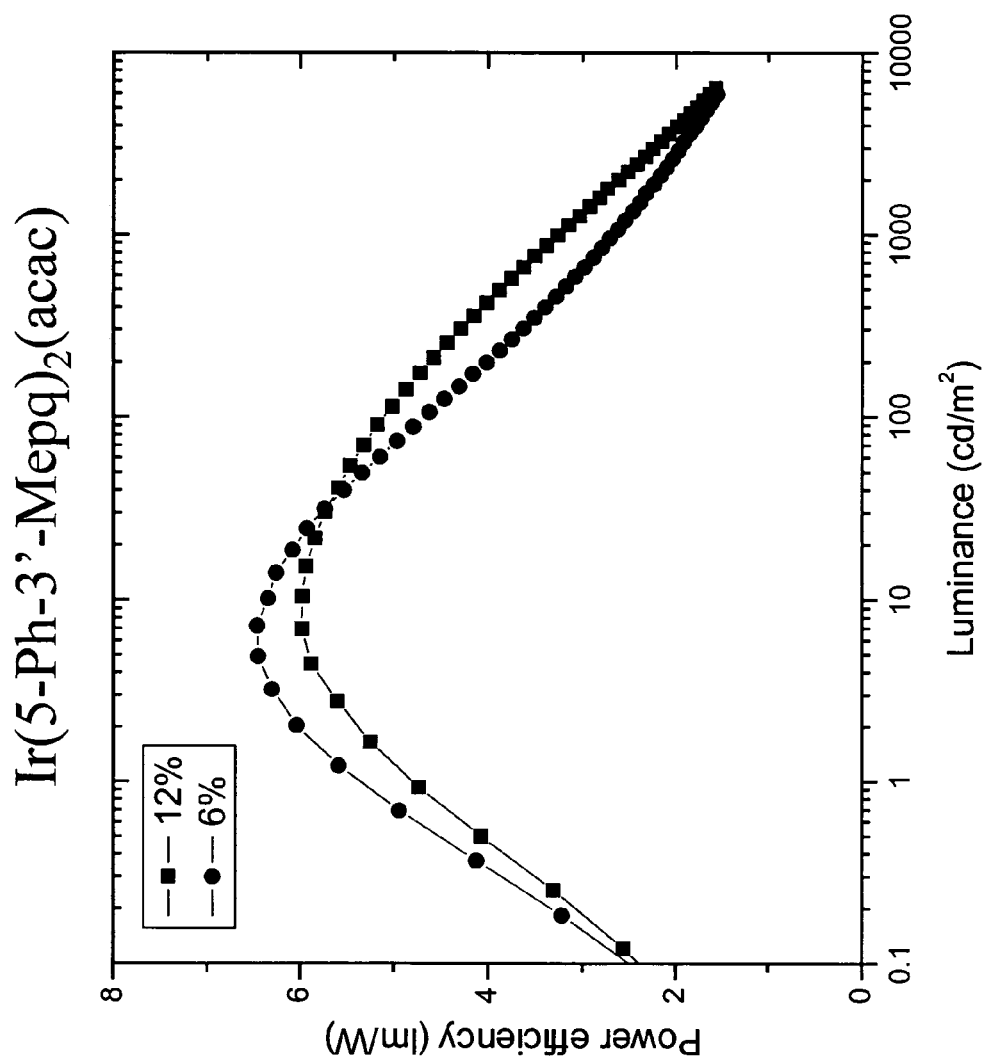
FIG. 5 shows plots of power efficiency (lm/W) vs. brightness (cd/m$^2$) for a Ir(5-Ph-3'-Mepq)$_2$(acac) device at dopant concentrations of 6% and 12%.
Figure 6:
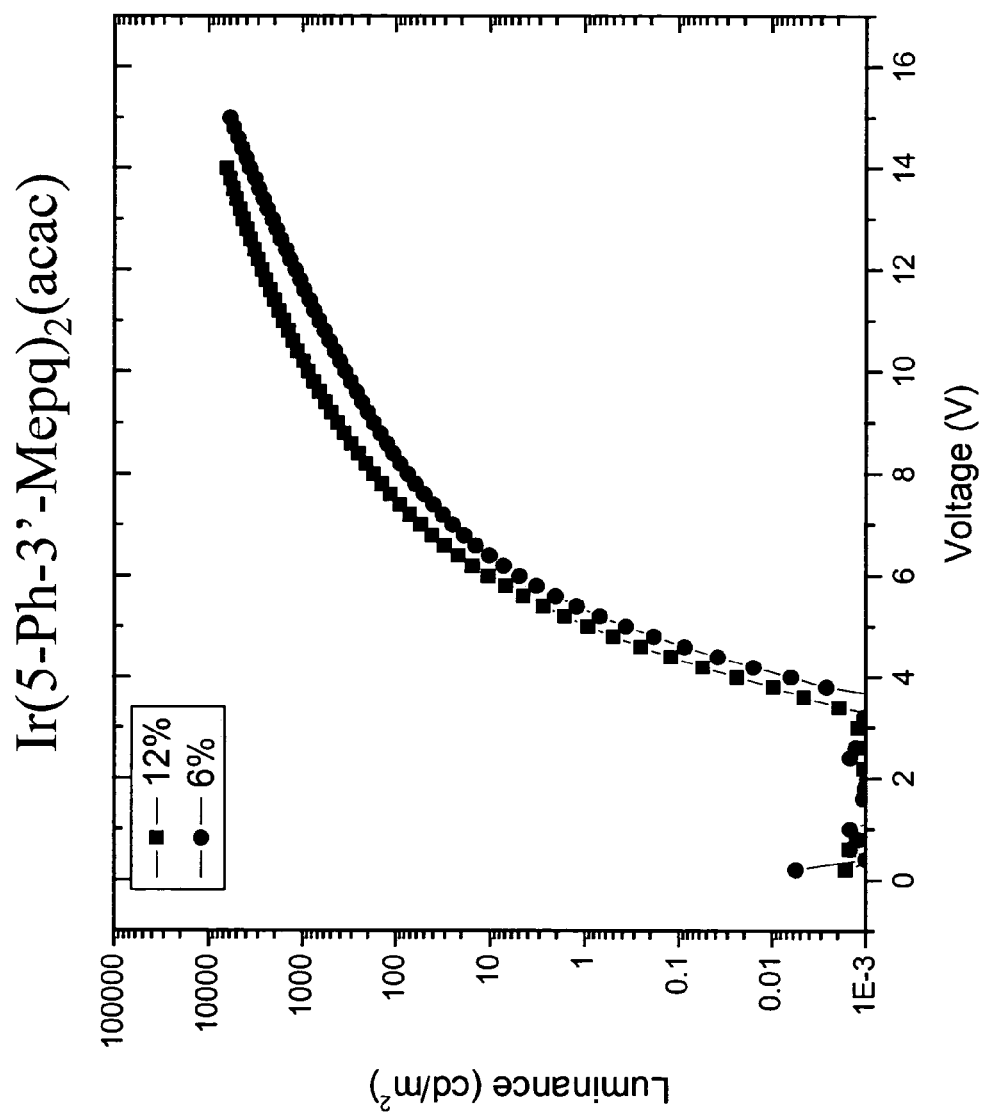
FIG. 6 shows plots of brightness (cd/m$^2$) vs. voltage for a Ir(5-Ph-3'-Mepq)$_2$(acac) device at dopant concentrations of 6% and 12%.
Figure 7:
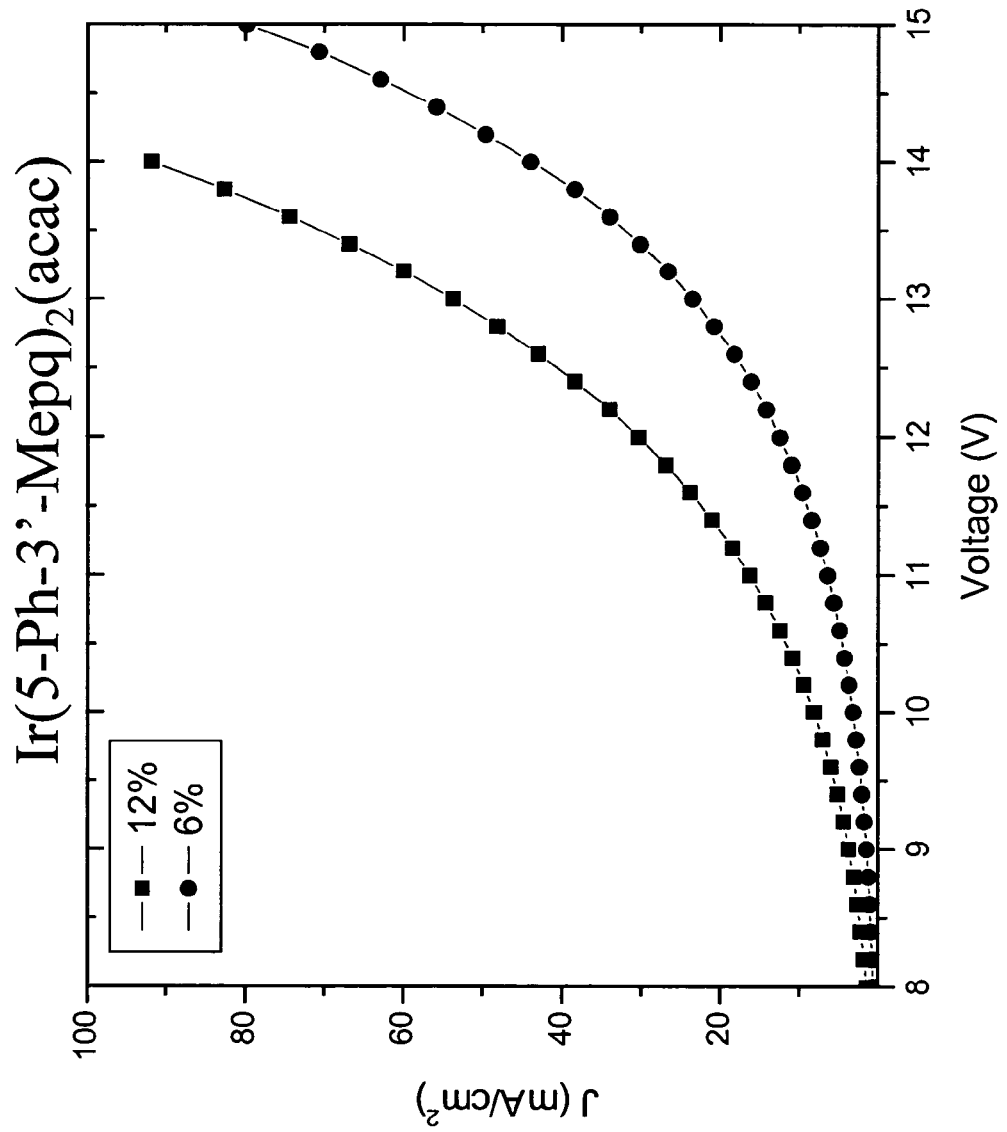
FIG. 7 shows the plots of the current density vs. the voltage for a Ir(5-Ph-3'-Mepq)$_2$(acac) device at dopant concentrations of 6% and 12% in a linear scale.
Figure 8:
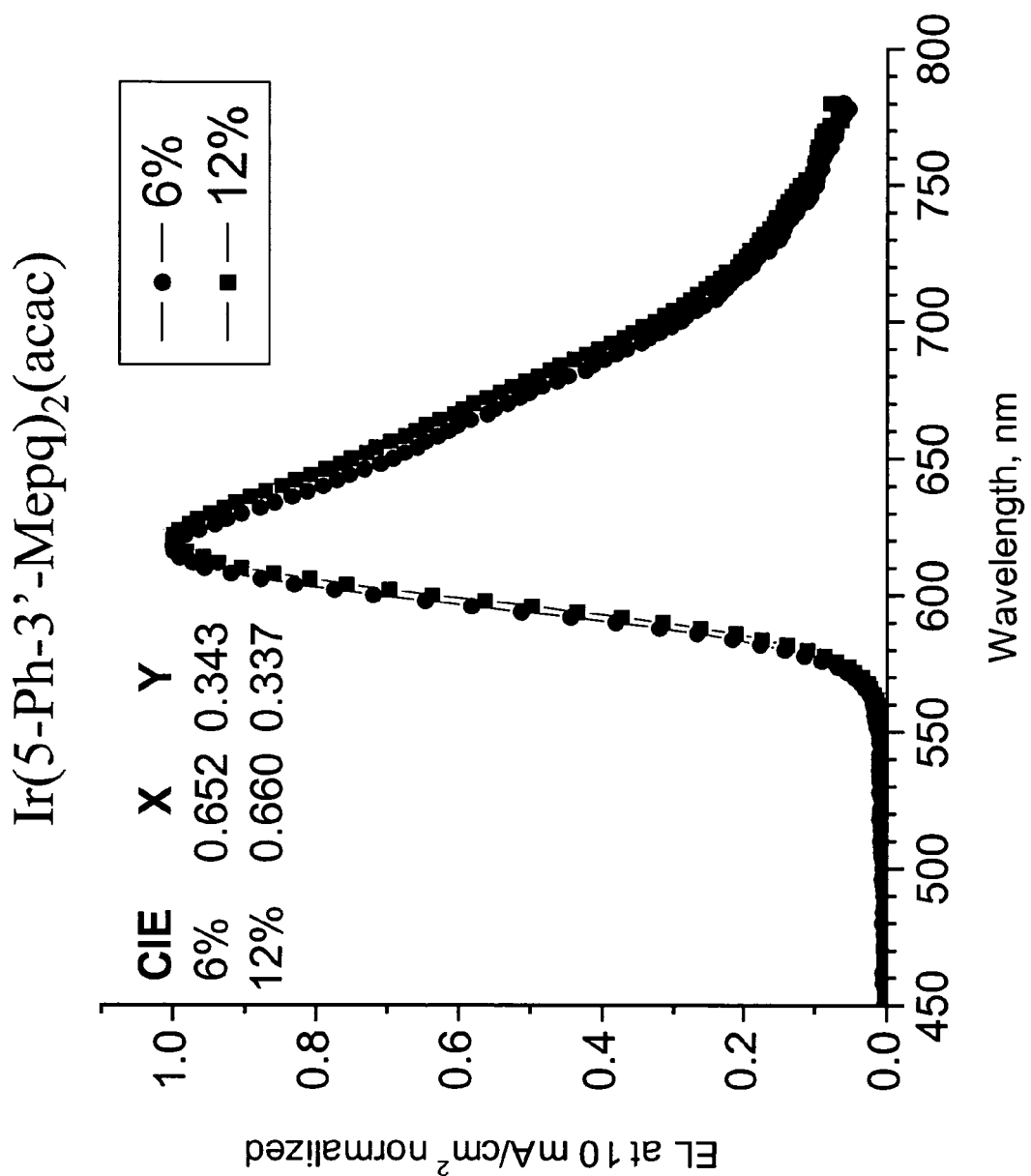
FIG. 8 shows a normalized electroluminescence spectra of a Ir(5-Ph-3'-Mepq)$_2$(acac) device at dopant concentrations of 6% and 12% and the corresponding CIE coordinates.
Figure 9:
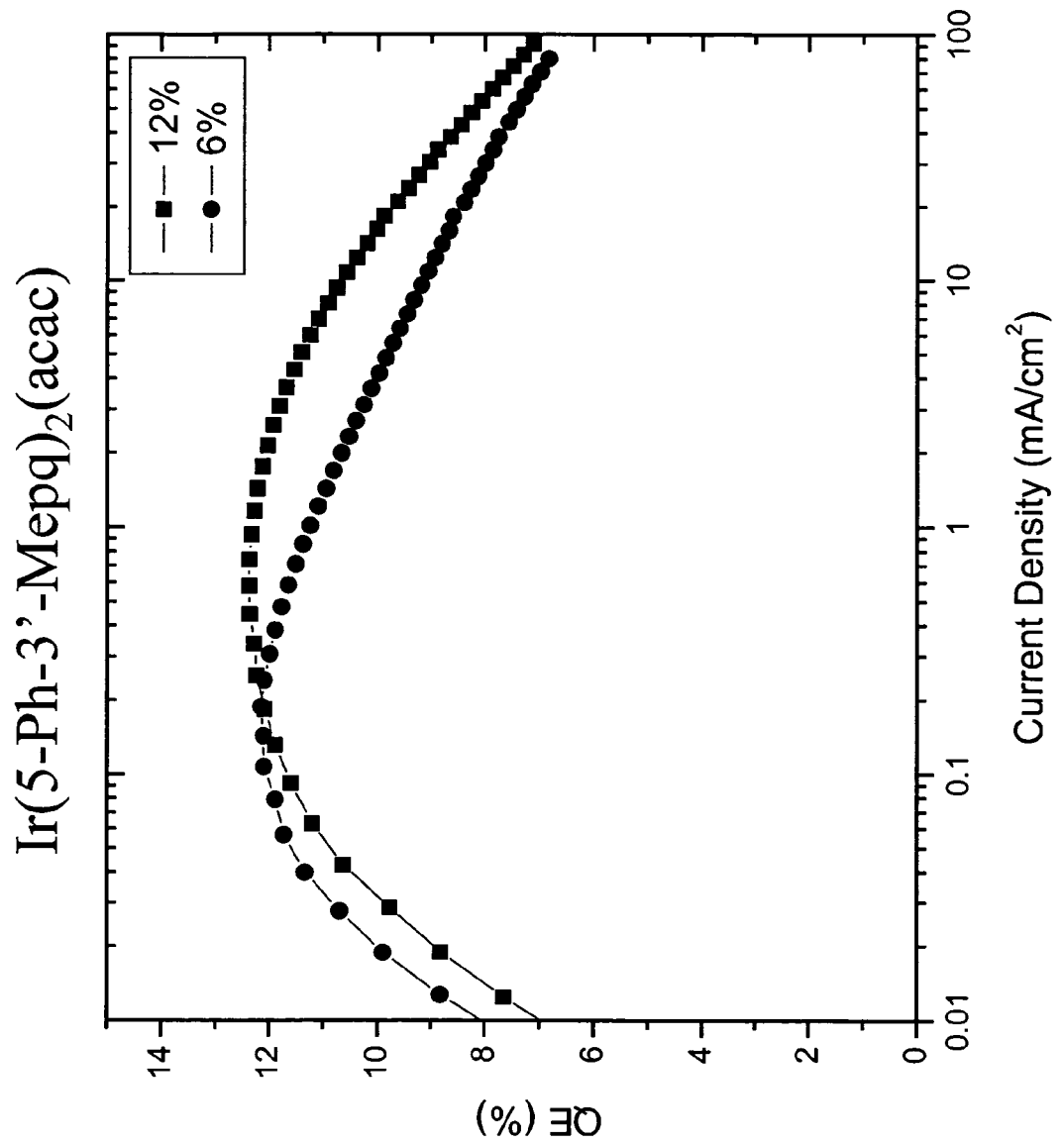
FIG. 9 shows the external quantum efficiency of a device vs. current density using Ir(5-Ph-3'-Mepq)$_2$(acac) as the emissive material doped at 6% and at 12%.
Figure 10:
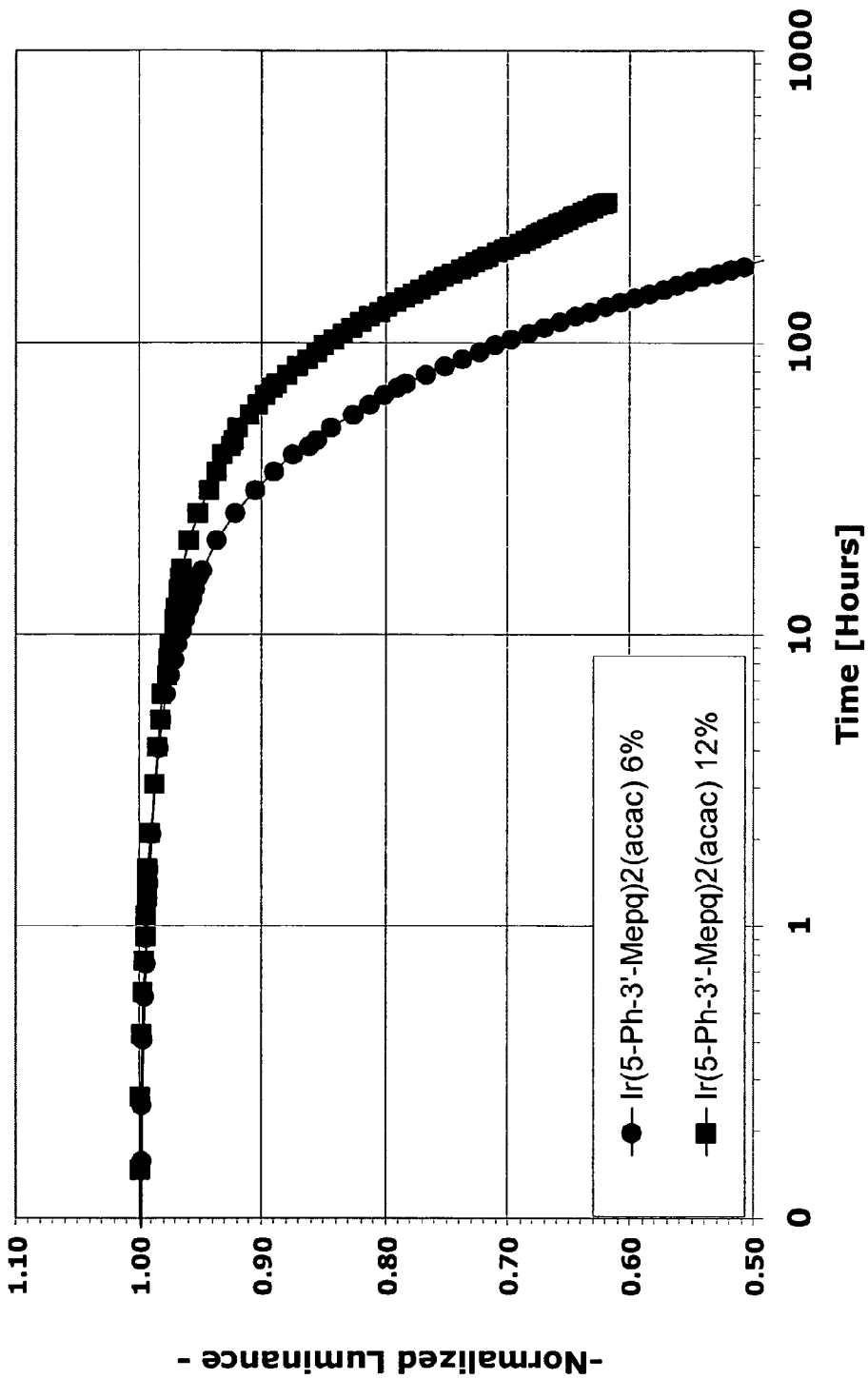
FIG. 10 shows normalized luminance decay for a Ir(5-Ph-3'-Mepq)$_2$(acac) device at dopant concentrations of 6% and at 12% under constant current drive of 40 mA/cm$^2$ at room temperature.
Figure 11:
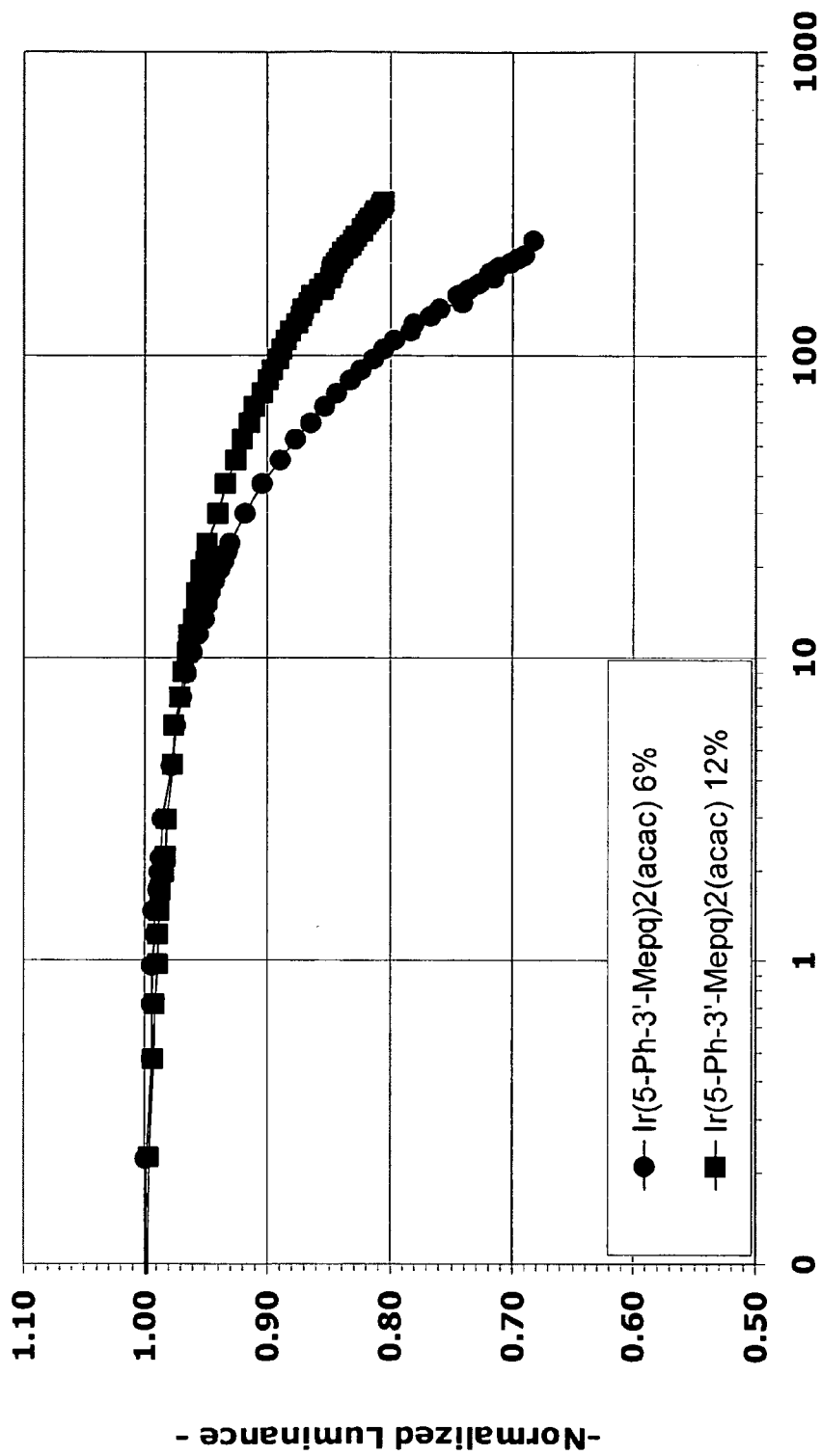
FIG. 11 shows plots of normalized luminance vs. time for a Ir(5-Ph-3'-Mepq)$_2$(acac) device at dopant concentrations of 6% and at 12% under constant current drive at 60° C. with an initial brightness of 480 cd/m$^2$.
Figure 12:
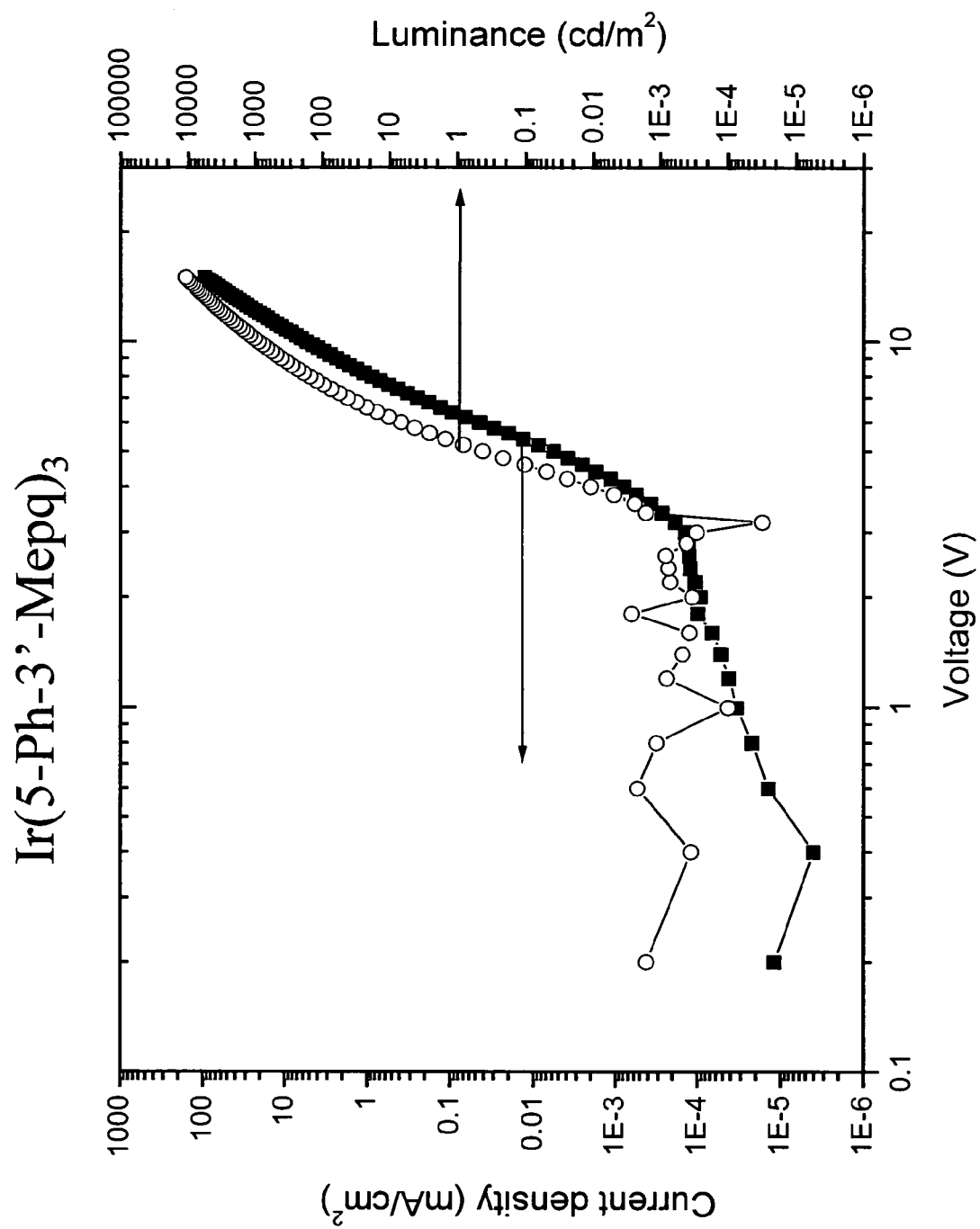
FIG. 12 shows plots of current density and brightness (cd/m$^2$) vs. voltage for a Ir(5-Ph-3'-Mepq)$_3$ device at a dopant concentration of 12%.
Figure 13:
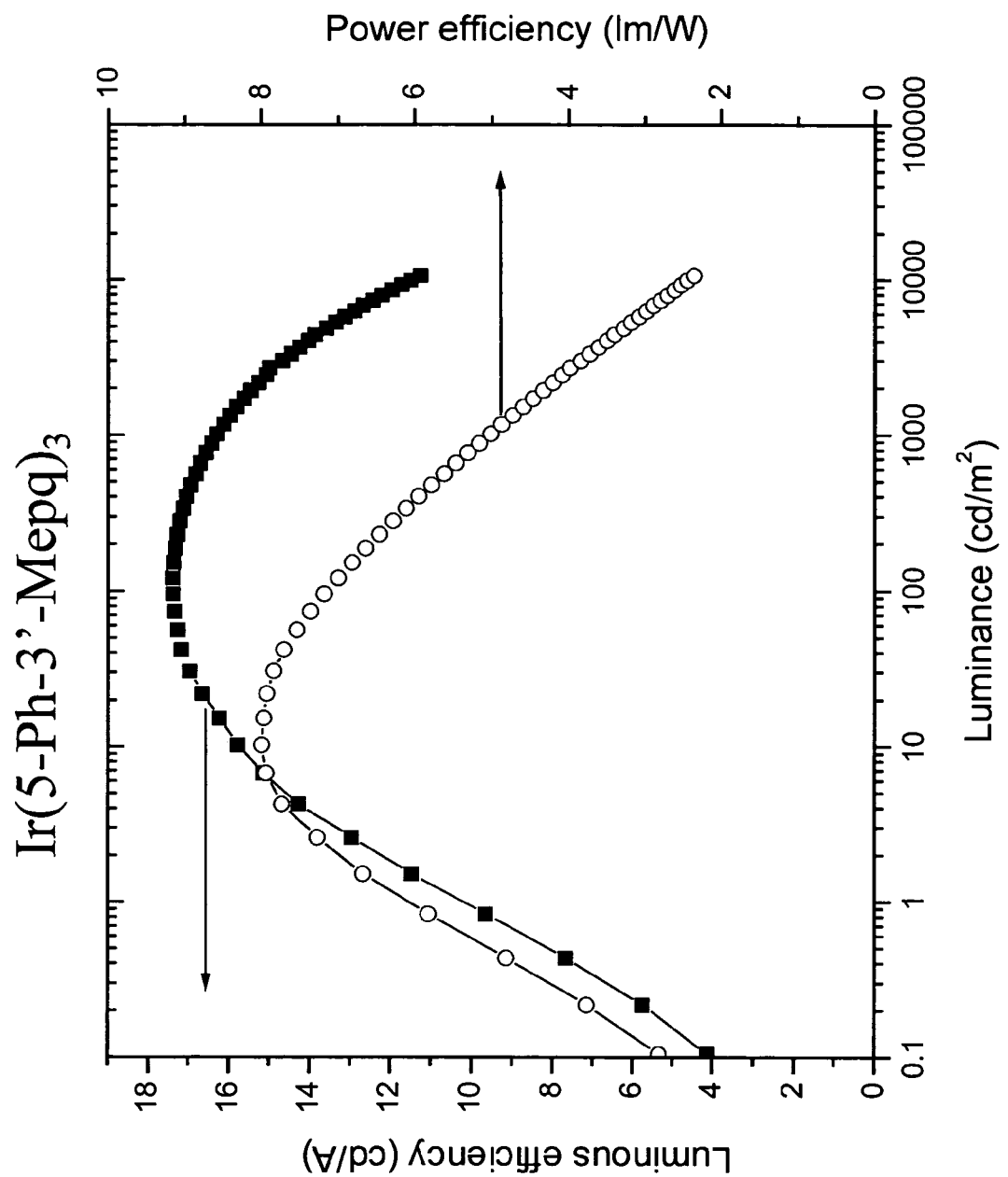
FIG. 13 shows plots of luminous efficiency (cd/A) and power efficiency (lm/W) vs. brightness (cd/m$^2$) for a Ir(5-Ph-3'-Mepq)$_3$ device at a dopant concentration of 12%.
Figure 14:
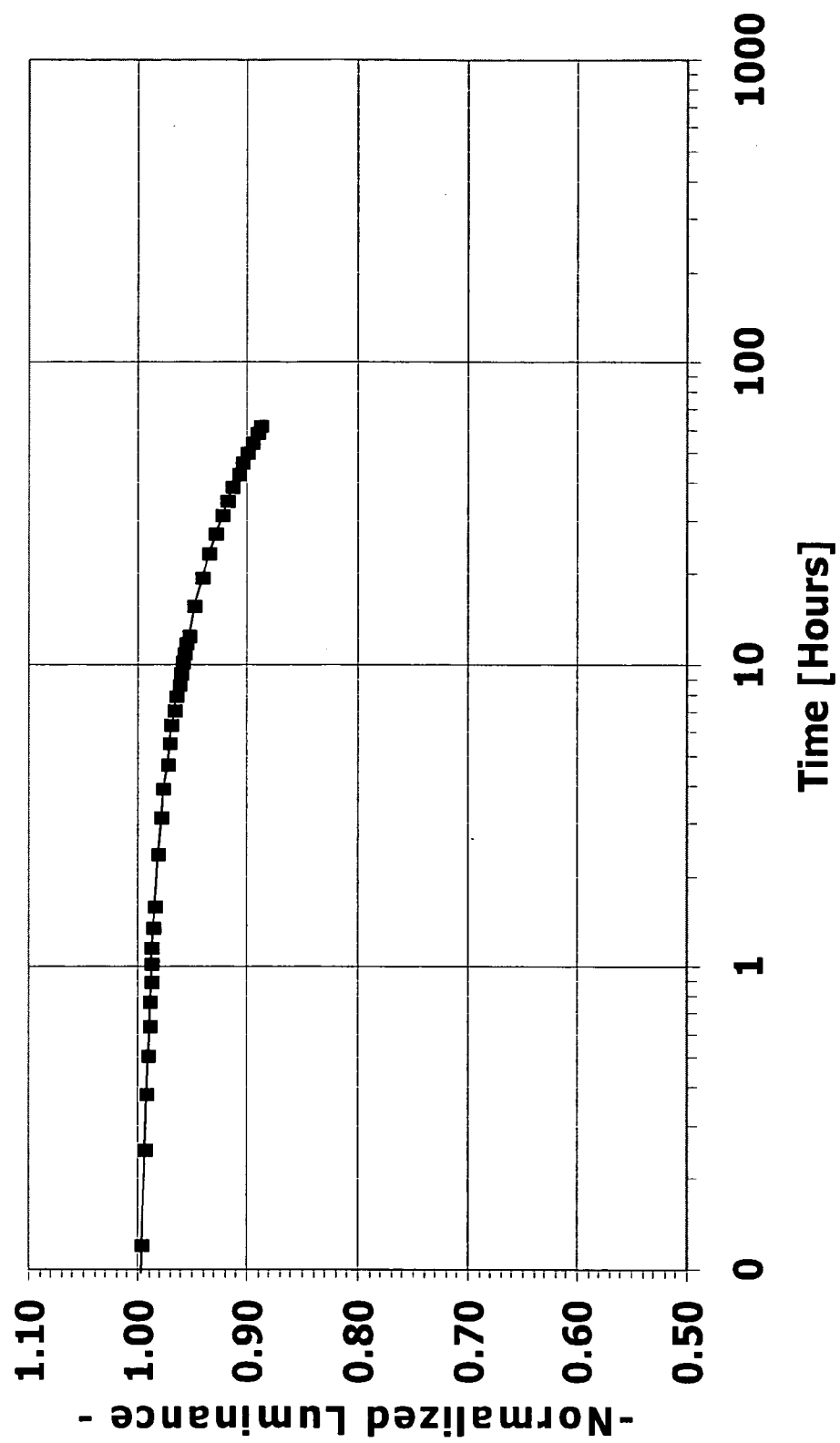
FIG. 14 shows normalized luminance decay for a Ir(5-Ph-3'-Mepq)$_3$ device at a dopant concentration of 12% under constant current drive of 40 mA/cm$^2$ at room temperature.
Figure 15:
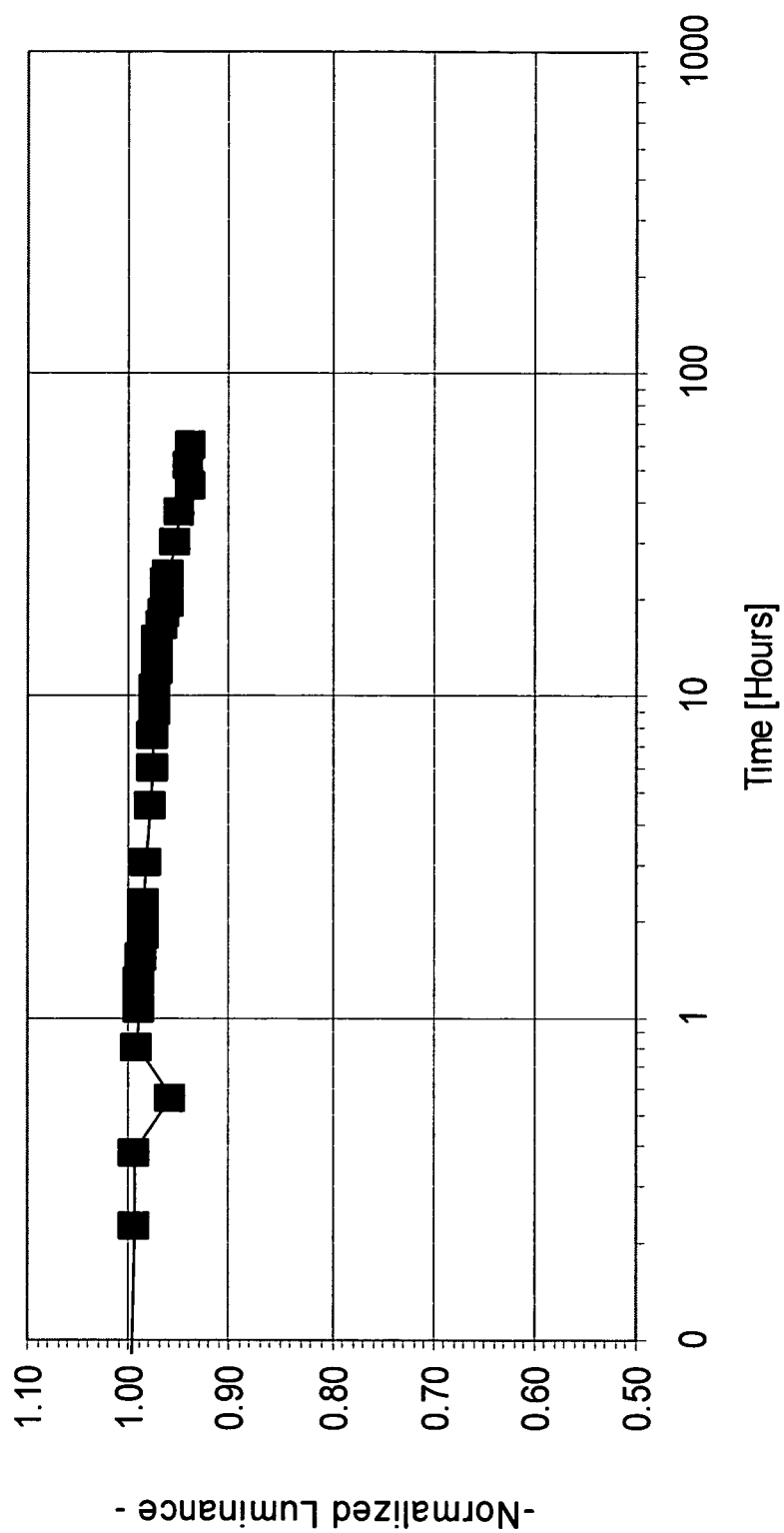
FIG. 15 shows plots of normalized luminance vs. time for a Ir(5-Ph-3'-Mepq)$_3$ device at a dopant concentration of 12% under constant current drive at 60° C. with an initial brightness of 480 cd/m$^2$.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

As used herein, "solution processible" means capable of being dissolved, dispersed, or transported in and/or deposited from a liquid medium, either in solution or suspension form.

"Stability" may be measured in a number of ways. One stability measurement is the operational stability of the electroluminescent device which can be measured in terms of operational half-life. The operational half-life is the time required for the luminance of the device to decay from the initial luminance ($L_0$) to 50% of its initial luminance ($L_{0.5}$) under constant current and at room temperature unless otherwise noted. Operational half-life depends upon luminance at which the device is operated, because a higher luminance generally corresponds to a faster decay in a particular device. Luminance may be measured in cd/m2. As shown in Table 1, the red and green emitting devices show the operational stability with under a constant direct current of 40 mA/cm$^2$ which corresponds to $L_0$>3000 cd/m$^2$ and $L_0$>9000 cd/m$^2$ for the red and green emitting devices respectively. When scaled to display operation brightness ($L_0$~300 cd/m$^2$ and 600 cd/m$^2$ for the red and green emitting devices respectively), the devices in accordance with embodiments of the present invention can advantageously have an operational half-life in excess of about 5000 hours.

In an embodiment of the present invention, a phosphorescent emissive material having improved efficiency when incorporated into an organic light emitting device is provided. The emissive material includes a photoactive ligand having the following structure:

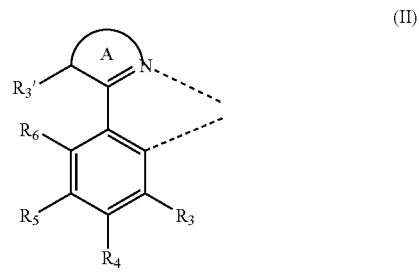

(II)

wherein

M is a metal having an atomic weight greater than 40;

$R_3'$ is a substituent selected from the group consisting of alkyl, heteroalkyl, aryl, heteroaryl, and aralkyl, wherein $R_3'$ is optionally substituted by one or more substituents Z;

$R_5$ is a substituent selected from the group consisting of aryl and heteroaryl, wherein said aryl or heteroaryl is unsubstituted or optionally, substituted with one or more non-aromatic groups;

ring A is an aromatic heterocyclic or a fused aromatic heterocyclic ring with at least one nitrogen atom that is coordinated to the metal M, wherein the ring A can be optionally substituted with one or more substituents Z;

$R_3$ is a substituent selected from the group consisting of H, alkyl, alkenyl, alkynyl, alkylaryl, CN, CF$_3$, C$_n$F$_{2n+1}$, trifluorovinyl, CO$_2$R, C(O)R, NR$_2$, NO$_2$, OR, halo, aryl, heteroaryl, substituted aryl, substituted heteroaryl or a heterocyclic group;

$R_4$ is a substitutent selected from the group consisting of H, alkyl, alkenyl, alkynyl, alkylaryl, CN, CF$_3$, C$_n$F$_{2n+1}$, trifluorovinyl, CO$_2$R, C(O)R, NR$_2$, NO$_2$, OR, halo, aryl, heteroaryl, substituted aryl, substituted heteroaryl or a heterocyclic group;

additionally or alternatively, $R_3$ and $R_4$, together from independently a fused 4 to 7-member cyclic group, wherein said cyclic group is cycloallcyl, cycloheteroalkyl, aryl, or heteroaryl; and wherein said cyclic group is optionally substituted by one or more substitutents Z;

$R_6$ is a substitutent selected from the group consisting of H, alkyl, alkenyl, alkynyl, alkylaryl, CN, CF$_3$, C$_n$F$_{2n+1}$, trifluorovinyl, $CO_2R$, $C(O)R$, $NR_2$, $NO_2$, OR, halo, aryl, heteroaryl, substituted aryl, substituted heteroaryl or a heterocyclic group;

alternatively, $R_3'$ and $R_6$ may be bridged by a group selected from $-CR_2-CR_2-$, $-CR=CR-$, $-CR_2-$, $-O-$, $-NR-$, $-O-CR_2-$, $-NR-CR_2-$, and $-N=CR-$;

each R is independently H, alkyl, alkenyl, alkynyl, heteroalkyl, aryl, heteroaryl, or aralkyl; wherein R is optionally substituted by one or more substituents Z;

each Z is independently a halogen, R', O—R', $N(R')_2$, SR', $C(O)R'$, $C(O)OR'$, $C(O)N(R')_2$, CN, $NO_2$, $SO_2$, SOR', $SO_2R'$, or $SO_3R'$;

each R' is independently H, alkyl, perhaloalkyl, alkenyl, alkynyl, heteroalkyl, aralkyl, aryl, or heteroaryl.

The term "halo" or "halogen" as used herein includes fluorine, chlorine, bromine and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted with one or more substituents selected from halo, CN, $CO_2R$, $C(O)R$, $NR_2$, cyclic-amino, $NO_2$, and OR.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted with one or more substituents selected from halo, CN, $CO_2R$, $C(O)R$, $NR_2$, cyclic-amino, $NO_2$, and OR.

The term "alkenyl" as used herein contemplates both straight and branched chain alkene radicals. Preferred alkenyl groups are those containing two to fifteen carbon atoms. Additionally, the alkenyl group may be optionally substituted with one or more substituents selected from halo, CN, $CO_2R$, $C(O)R$, $NR_2$, cyclic-amino, $NO_2$, and OR.

The term "alkynyl" as used herein contemplates both straight and branched chain alkyne radicals. Preferred alkyl groups are those containing two to fifteen carbon atoms. Additionally, the alkynyl group may be optionally substituted with one or more substituents selected from halo, CN, $CO_2R$, $C(O)R$, $NR_2$, cyclic-amino, $NO_2$, and OR.

The terms "alkylaryl" as used herein contemplates an alkyl group that has as a substituent an aromatic group. Additionally, the alkylaryl group may be optionally substituted on the aryl with one or more substituents selected from halo, CN, $CO_2R$, $C(O)R$, $NR_2$, cyclic-amino, $NO_2$, and OR.

The term "heterocyclic group" as used herein contemplates non-aromatic cyclic radicals. Preferred heterocyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like.

The term "aryl" or "aromatic group" as used herein contemplates single-ring groups and polycyclic ring systems. The polycyclic rings may have two or more rings in which two carbons are common by two adjoining rings (the rings are "fused") wherein at least one of the rings is aromatic, e.g., the other rings can be cycloalkyls, cycloalkenyls, aryl, heterocycles and/or heteroaryls.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles and/or heteroaryls.

All value ranges, for example those given for n and m, are inclusive over the entire range. Thus, for example, a range between 0-4 would include the values 0, 1, 2, 3 and 4.

This ligand is referred to as "photoactive" because it is believed that it contributes to the photoactive properties of the emissive material. The emissive material comprises at least one photoactive ligand of the formula II and a heavy metal ion such that the resulting material has (i) a carbon-metal bond and (ii) the nitrogen of ring A is coordinated to the metal. Thus the emissive materials of the present invention comprise a partial structure of formula

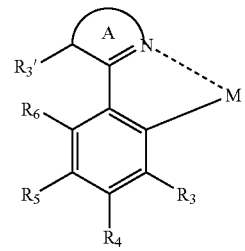

M may be any metal having an atomic weight greater than 40. Preferred metals include Ir, Pt, Pd, Rh, Re, Os, Tl, Pb, Bi, In, Sn, Sb, Te, Au, and Ag. More preferably, the metal is Ir or Pt. Most preferably, the metal is Ir.

In another embodiment of the invention, the emissive material has the formula

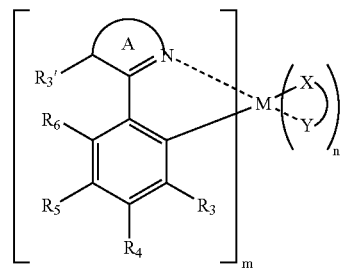

m, the number of photoactive ligands of a particular type, may be any integer from 1 to the maximum number of ligands that may be attached to the metal. For example, for Ir, m may be 1, 2 or 3. n, the number of "ancillary" ligands of a particular type, may be any integer from zero to one less than the maximum number of ligands that may be attached to the metal. (X—Y) represents an ancillary ligand. These ligands are referred to as "ancillary" because it is believed that they may modify the photoactive properties of the molecule, as opposed to directly contributing to the photoactive properties. The definitions of photoactive and ancillary are intended as non-limiting theories. For example, for Ir, n may be 0, 1 or 2 for bidentate ligands. Ancillary ligands for use in the emissive material may be selected from those known in the art. Non-limiting examples of ancillary ligands may be found in PCT Application Publication WO 02/15645 A1 to Lamansky et al. at pages 89-90, which is incorporated herein by reference. Preferred ancillary ligands include acetylacetonate (acac) and picolinate (pic), and derivatives thereof. The preferred ancillary ligands have the following structures:

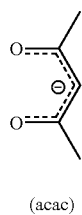 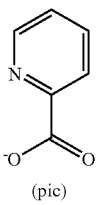

(acac) (pic)

In a preferred embodiment, the ring A of the photoactive ligand is pyridine, giving a ligand of the formula:

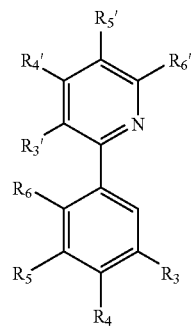

and a partial structure for the emissive material of the formula:

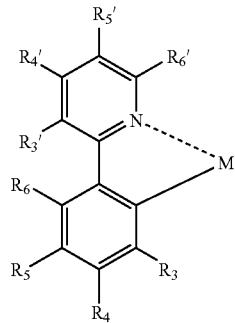

An embodiment of the invention includes a molecule with the following structure:

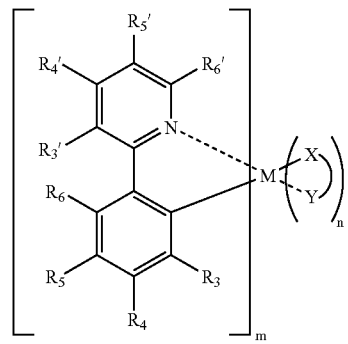

Another embodiment of the present invention has a ligand structure with the following formula:

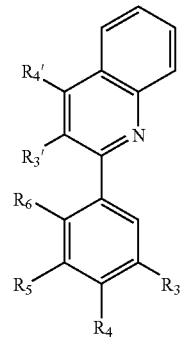

and a partial structure for the emissive material of the formula:

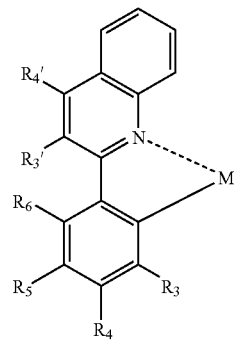

This embodiment of the invention includes a molecule with the following structure:

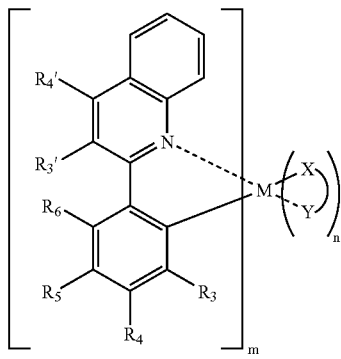

$R_3$, $R_4$, $R_5$, $R_6$, $R_3'$ and $R_4'$ are defined according to the definitions of Formula II. The remaining positions on the quinoline ring can be optionally substituted.

Another embodiment of the present invention has a ligand structure with the following formula:

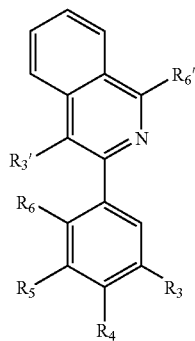

and a partial structure for the emissive material of the formula:

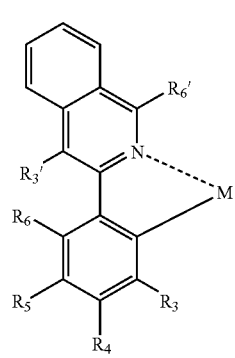

This embodiment of the invention includes a molecule with the following structure:

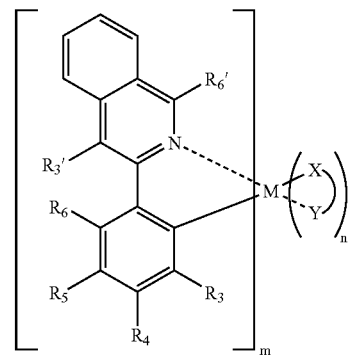

$R_3$, $R_4$, $R_5$, $R_6$, $R_3'$, and $R_6'$ are defined according to the definitions of Formula II. The remaining positions on the isoquinoline ring can be optionally substituted.

Another embodiment of the present invention has a ligand structure with the following formula:

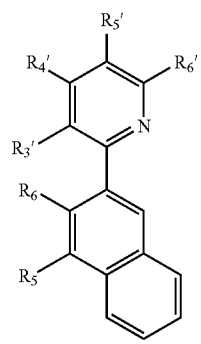

and a partial structure for the emissive material of the formula:

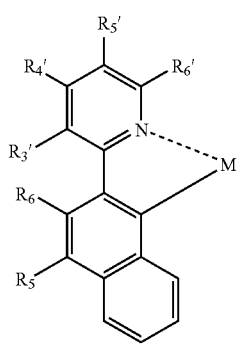

This embodiment of the invention includes a molecule with the following structure:

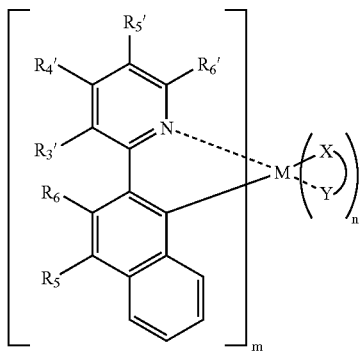

$R_5$, $R_6$, $R_3'$, $R_4'$, $R_5'$, and $R_6'$ are defined according to the definitions of Formula II. The remaining positions on the naphthyl ring can be optionally substituted.

In another preferred embodiment, the substituent $R_5$ of the photoactive ligand is phenyl, and $R_3'$ is methyl, giving a ligand of the formula:

(III)

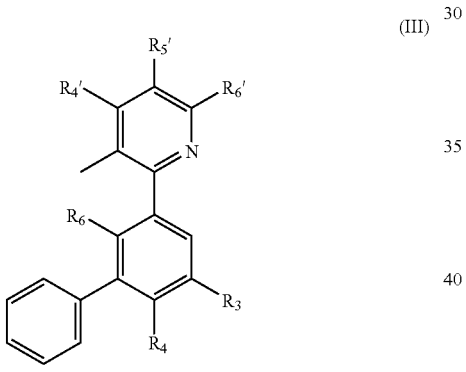

and a partial structure for the emissive material of the formula:

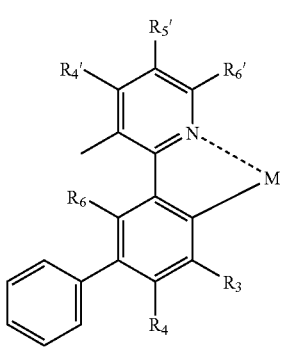

This embodiment of the invention includes a molecule with the following structure:

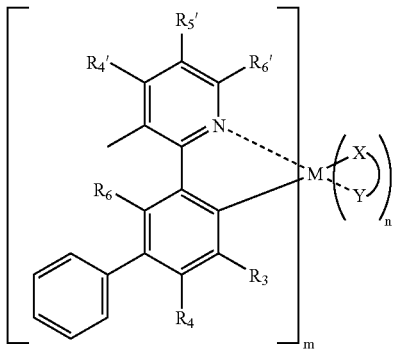

$R_3$, $R_4$, $R_6$, $R_4'$, $R_5'$, and $R_6'$ are defined according to the definitions of Formula II.

In another preferred embodiment, n is zero, and m is the maximum number of ligands that may be attached to the metal.

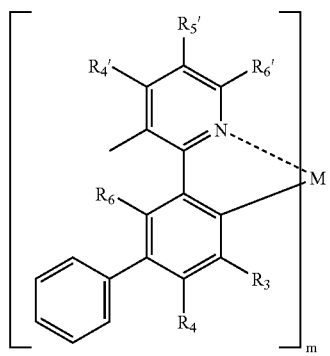

For example, for Ir, m is three in this preferred embodiment, and the structure may be referred to as a "tris" structure. The tris structure is preferred because it is believed to be particularly stable. $R_3$, $R_4$, $R_6$, $R_4'$, $R_5'$, and $R_6'$ are defined according to the definitions of Formula II.

In one embodiment, m+n is equal to the total number of bidentate ligands that may be attached to the metal in question—for example, 3 for Ir. In another embodiment, m+n may be less than the maximum number of bidentate ligands that may be attached to the metal, in which case other ligands—ancillary, photoactive, or otherwise—may also be attached to the metal. Preferably, if there are different photoactive ligands attached to the metal, each photoactive ligand has the structure indicated in Formula II.

In another embodiment of the present invention, M is Ir and m is 3, giving an emissive material of the formula:

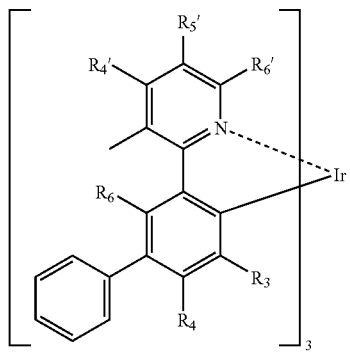

$R_3$, $R_4$, $R_6$, $R_4'$, $R_5'$, and $R_6'$ are defined according to the definitions of Formula II.

In a more preferred embodiment, $R_3=R_4=R_6=R_4'=R_5'=R_6'=H$. The emissive material of this embodiment has the following structure of formula:

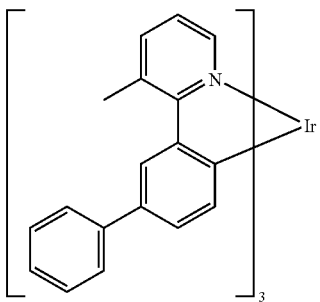

$R_3$, $R_4$, $R_6$, $R_4'$, $R_5'$, and $R_6'$ are defined according to the definitions of Formula II.

In another more preferred embodiment, $R_5'$ and $R_6'$ form a fused 6 member aryl ring, and $R_3=R_4=R_6=R_4'=H$. The emissive material of this embodiment has the following structure of formula:

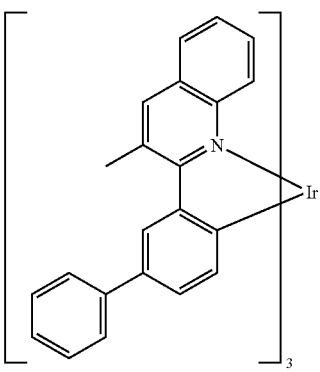

$R_3$, $R_4$, $R_6$, and $R_4'$ are defined according to the definitions of Formula II.

In another preferred embodiment of the present invention, M is Ir, m is 2, n is 1, and the ancillary ligand (X—Y) is acac, giving an emissive material of the formula:

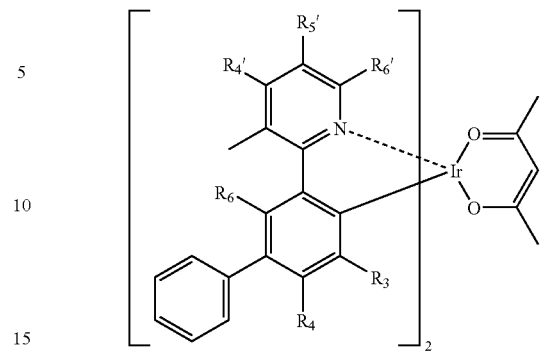

$R_3$, $R_4$, $R_6$, $R_4'$, $R_5'$, and $R_6'$ are defined according to the definitions of Formula II.

In a more preferred embodiment, $R_3=R_4=R_6=R_4'=R_5'=R_6'=H$. The material of this embodiment has the following structure of formula:

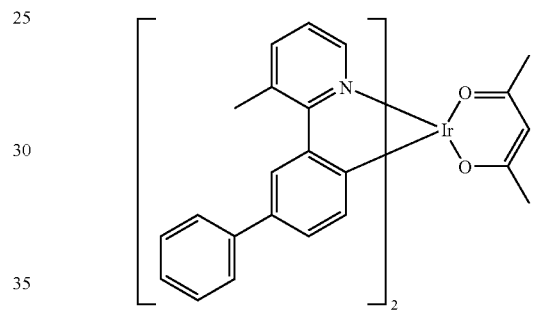

$R_3$, $R_4$, $R_6$, and $R_4'$, $R_5'$, and $R_6'$ are defined according to the definitions of Formula II.

In another more preferred embodiment, $R_5'$ and $R_6'$ form a fused 6 member aryl ring, and $R_3=R_4=R_6=R_4'=H$. The emissive material of this embodiment has the following structure of formula:

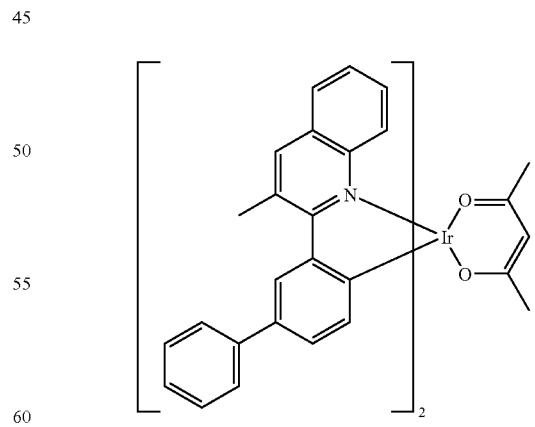

$R_3$, $R_4$, $R_6$, and $R_4'$ are defined according to the definitions of Formula II.

Without being limited to any theory as to how the invention works, it is believed that the combination of $R_3'$ and $R_5$ as disclosed in Formula II leads to an emissive material having enhanced stability. In particular, it is believed that the specific substituents shown in Formula III provide a particularly stable molecule, i.e., $R_5$ is phenyl and $R_3'$ is methyl, both unsubstituted. It is further believed that the enhanced stability is still present if the phenyl and/or methyl in the $R_5$ and $R_3'$ positions, respectively, are substituted. In addition, substitution at the $R_3'$ position has been shown to increase device lifetime. Substitution at the $R_5$ position has also been shown to increase device lifetime, as disclosed in U.S. patent application Ser. No. 10/289,915 to Brown et al., which is incorporated by reference in its entirety. In the present invention, substitutions at both the $R_3'$ and $R_5$ positions show a further improvement in the lifetime of the device than substitution for only the $R_3'$ or the $R_5$ position.

It is understood that the various embodiments described herein are by way of example only, and are not intended to limit the scope of the invention. For example, many of the materials and structures described herein may be substituted with other materials and structures without deviating from the spirit of the invention. It is understood that various theories as to why the invention works are not intended to be limiting. For example, theories relating to charge transfer are not intended to be limiting.

Material Definitions:

As used herein, abbreviations refer to materials as follows:

| | |
|---|---|
| CBP: | 4,4'-N,N-dicarbazole-biphenyl |
| m-MTDATA | 4,4',4''-tris(3-methylphenylphenlyamino)triphenylamine |
| Alq$_3$: | 8-tris-hydroxyquinoline aluminum |
| Bphen: | 4,7-diphenyl-1,10-phenanthroline |
| n-BPhen: | n-doped BPhen (doped with lithium) |
| F$_4$-TCNQ: | tetrafluoro-tetracyano-quinodimethane |
| p-MTDATA: | p-doped m-MTDATA (doped with F$_4$-TCNQ) |
| Ir(ppy)$_3$: | tris(2-phenylpyridine)-iridium |
| Ir(ppz)$_3$: | tris(1-phenylpyrazoloto,N,C(2')iridium(III) |
| BCP: | 2,9-dimethyl-4,7-diphenyl-1,10-phenanthroline |
| TAZ: | 3-phenyl-4-(1'-naphthyl)-5-phenyl-1,2,4-triazole |
| CuPc: | copper phthalocyanine. |
| ITO: | indium tin oxide |
| NPD: | N,N'-diphenyl-N-N'-di(1-naphthyl)-benzidine |
| TPD: | N,N'-diphenyl-N-N'-di(3-toly)-benzidine |
| BAlq: | aluminum(III)bis(2-methyl-8-quinolinato) 4-phenylphenolate |
| mCP: | 1,3-N,N-dicarbazole-benzene |
| DCM: | 4-(dicyanoethylene)-6-(4-dimethylaminostyryl-2-methyl)-4H-pyran |
| DMQA: | N,N'-dimethylquinacridone |
| PEDOT:PSS: | an aqueous dispersion of poly(3,4-ethylenedioxythiophene) with polystyrenesulfonate (PSS) |

EXPERIMENTAL

Specific representative embodiments of the invention will now be described, including how such embodiments may be made. It is understood that the specific methods, materials, conditions, process parameters, apparatus and the like do not necessarily limit the scope of the invention.

EXAMPLE 1

Synthesis of Bis[5-phenyl-3'-methyl(2phenylquinoline)]iridium Acetylacetonate [Ir(5-Ph-3'-Mepq)$_2$(acac)]

Step 1 Synthesis of 3-Biphenylboronic Acid (3)

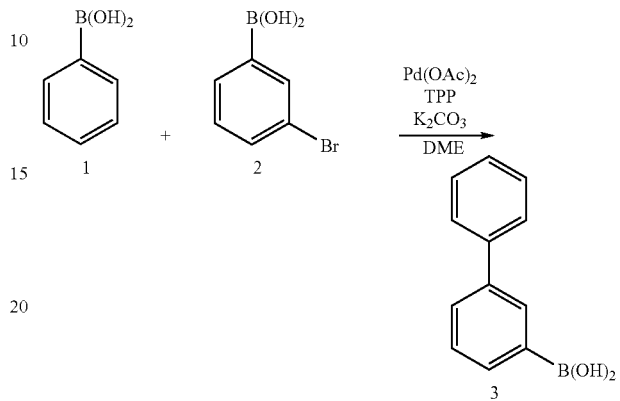

Phenyl boronic acid (1) (106.2 g, 871.4 mmol), 3-bromophenylboronic acid (2) (35.0 g, 174.2 mmol), palladium acetate (9.8 g, 4.357 mmol), triphenylphosphine (4.64 g, 17.4 mmol), and 2M K$_2$CO$_3$ aqueous solution (470 ml) were added to 950 mL of dimethoxyethane and refluxed for 17 hours. The mixture was cooled to room temperature and the aqueous layer was separated from the organic layer. The aqueous layer was then extracted twice with 200 mL of ethyl acetate. The organic layers were combined and washed with brine and dried over magnesium sulfate. The solids were removed by vacuum filtration and the organic solvent evaporated to the crude product. The crude product was purified by Kugelehor distillation to give of 3 (30 g, 86.7%).

Step 2 Synthesis of 5-phenyl-3'-methyl(2-phenylquinoline) (5)

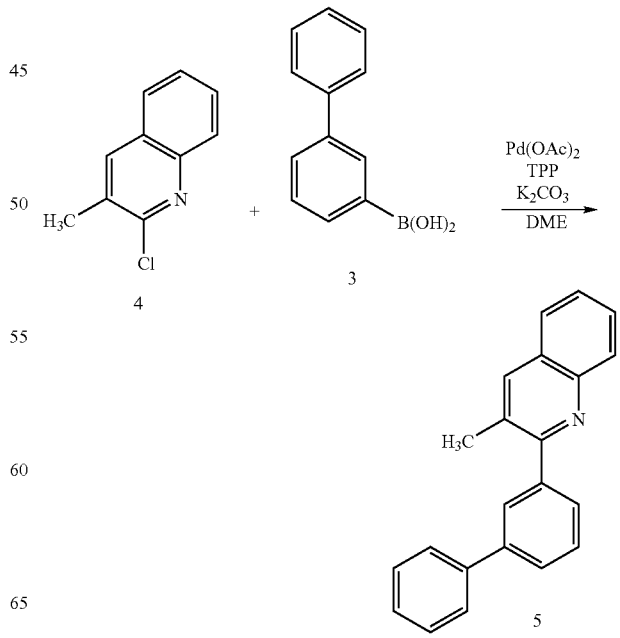

A mixture of 2-chloro-3-methylquinoline (4) (14.7 g, 0.09 mol), 3-biphenylbornic acid (3) (21.3 g, 0.11 mol), palladium acetate (0.5 g, 2.24 mmol), triphenylphosphine (2.4 g, 8.96 mmol), K$_2$CO$_3$ (121 mL, 2M solution), and 1,2-dimethoxyethane (132 mL) was heated to 80° C. for 10 hours under N$_2$. The cooled mixture was poured into 200 mL water and extracted by ethyl acetate (100 mL×3). The organic layer was washed by brine and dried over MgSO$_4$. The solvent was evaporated and the residue was subjected to Kugelrohr distillation at 220° C. at 170 micro to yield 5 (20 g, 84%).

Step 3 Synthesis of Bis[5-phenyl-3'-methyl(2-phenylquinoline)]iridium Dichloro Bridge Dimer (6)

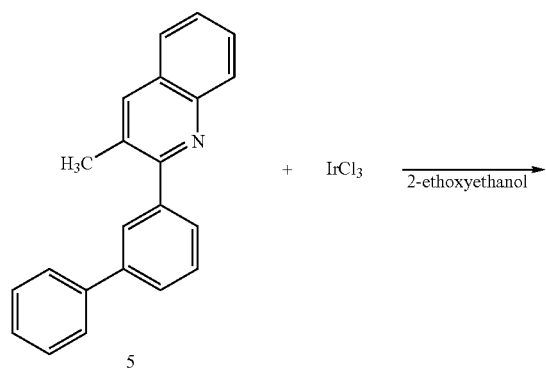

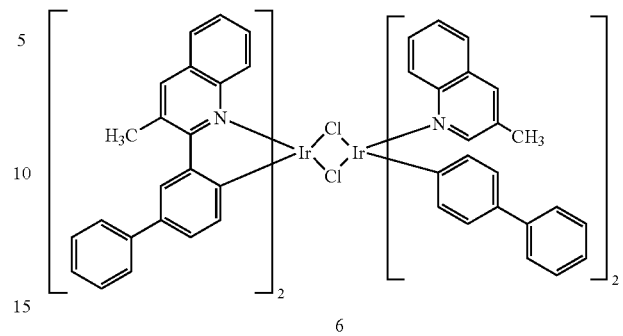

Compound 5 (15 g, 50.82 mmol, 2 equiv.) was added to 120 mL of 2-ethoxyethanol and the solution was stirred. IrCl$_3$.4H$_2$O (9.418 g, 25.4 mmol, 2 equiv.) was then added to the stirred solution. The reaction was heated at 132° C. and stirred for 90 hours under N$_2$ purge. The solution was cooled and filtered. The reddish solid was washed with ethanol twice and dried in vacuum to give crude compound 6. It was redissolved in methylene chloride (~1300 mL) and filtered. The collected filtrate was dried to get 6 (14.57 g, 70%).

Step 4 Synthesis of Bis[5-phenyl-3'-methyl(2-phenylquinoline)]iridium Acetylacetonate [Ir(5-Ph-3'-Mepq)$_2$(acac)]

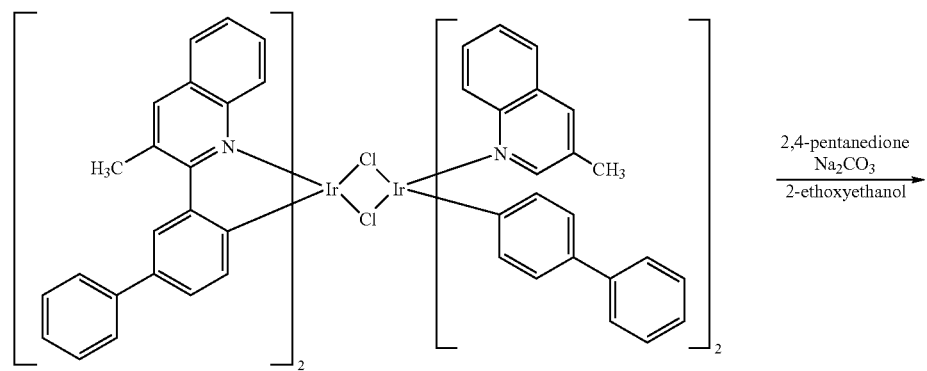

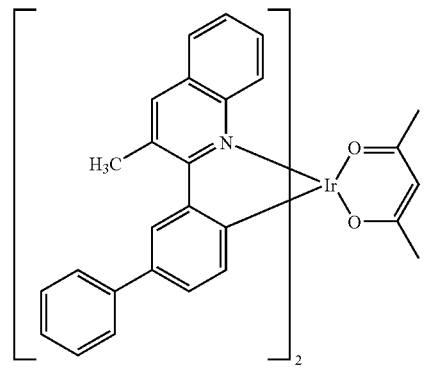

Ir(5-Ph-3'Mepq)$_2$(acac)

6 (14.57 g, 8.93 mmol), 2,4-pentanedione (8.9 g, 89.3 mmol), and sodium carbonate (18.93 g, 178.6 mmol) were added to 116 mL of 2-ethoxyethanol and the mixture was heated at 100° C. for 16 hours under a nitrogen atmosphere. The cooled mixture was then filtered. The collected precipitate was added to 500 mL of water and stirred for 1 hour. This mixture was then vacuum filtered and washed with methanol to give product. It was then purified on a silca gel column using methylene chloride as the eluant. The fractions were collected and the solvent evaportated to give Ir(5-Ph-3'-Mepq)$_2$(acac) (9.83 g, 62%).

EXAMPLE 2

Synthesis of Tis[5-phenyl-3'-methyl(2-phenylquinoline)]iridium [Ir(5-Ph-3'-Mepq)$_3$]

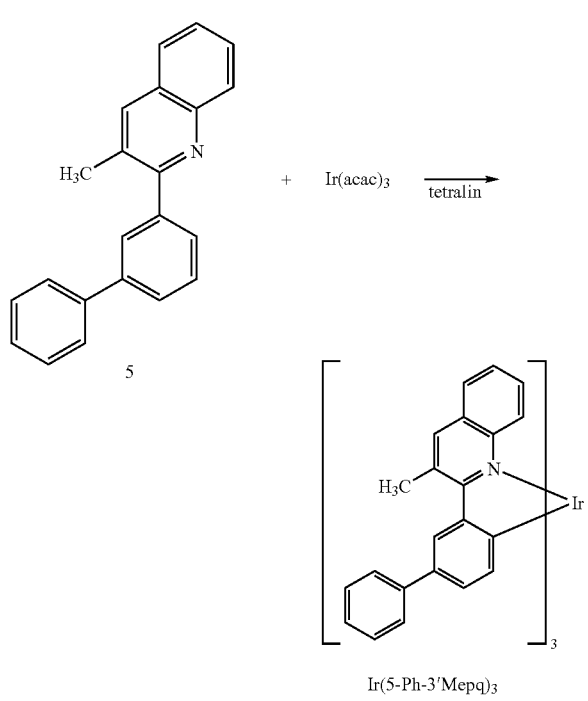

Ir(5-Ph-3'Mepq)$_3$

To a 250 mL (HEL low pressure auto-mate reactor system) with nitrogen atmosphere was added 50 mL of tetralin, 1.82 g (0.0038 mol) of tris(acetylacetonate)iridium (III) and 16.47 g of 5 (0.0558 mol) and heated to 190° C.-225° C. for 16 days. The reaction mixture/slurry was cooled to 45° C.-50° C., diluted with 30 mL of methylene chloride and excess 5 was removed. The combined mother liquor was concentrated at the rotovap at 85° C.-90° C. to give 40.16 g of a crude dark oil containing Ir(5-Ph-3'-Mepq)$_3$. The crude product mixture was filtered through a plug of silica gel and flushed with toluene. The combined mother liquor and toluene washes from the silica column were concentrated at the rotovap to give 38.4 g of a crude oil containing Ir(5-Ph-3'-Mepq)$_3$. On standing, the oil deposited crystals which were diluted with cyclohexane and isolated to give 4.72 g of 5. The combined mother liquors were again concentrated at the rotary evaporator to give 32.84 g of dark oil that was vacuum distilled to give 21.7 g of distillate containing about 84% naphthalene and 13% tetralin and a pot residue of about 7.6 g of tar containing Ir(5-Ph-3'-Mepq)$_3$. The 7.6 g of product tar was dissolved in methylene chloride, transferred to a column of silica gel and eluted with a mixture of 50/50 v/v methylene chloride/hexanes. Several fractions were collected and those that contained Ir(5-Ph-3'-Mepq)$_3$ were individually concentrated at the rotary evaporator as previously to give 2.4 g and 0.35 g respectively. To the combined 2.75 g of crude Ir(5-Ph-3'-Mepq)$_3$ concentrate was added toluene. The mixture was heated to 90° C. on the water bath to dissolve residual naphthalene, cooled and red solids were isolated to deliver 0.74 g of crude Ir(5-Ph-3'-Mepq)$_3$. Subsequently, 0.69 g of product was recrystallized from a small volume of DMF. The bright red Ir(5-Ph-3'-Mepq)$_3$ was collected and washed with 3×5 mL of toluene and followed with 3×10 mL of hexanes. The product Ir(5-Ph-3'-Mepq)$_3$ was vacuum dried at 98° C. and delivered 0.5 g as red solids.

EXAMPLE 3

Synthesis of Bis[5-phenyl-3'-methyl(2-phenylpyridine)]iridium acetylacetonate [Ir(5-Ph-3'-Meppy)$_2$(acac)]

Step 1 5-phenyl-3'-methyl(2-phenylpyridine) (10)

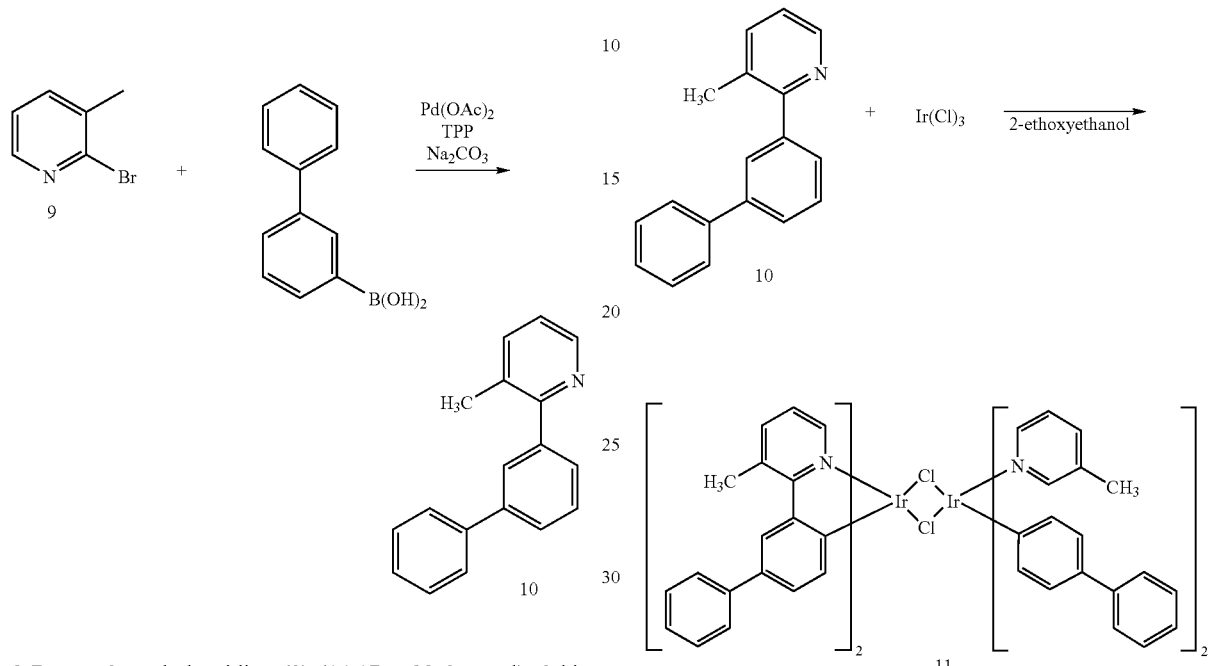

2-Bromo-3-methylpyridine (9) (14.17 g 82.6 mmol), 3-biphenylboronic acid (3) (13.8 g, 69.7 mmol), triphenylphosphine, (1.52 g, 5.7 mmol), Na$_2$CO$_3$ (16.64 g, 157.0 mmol) and palladium (II) acetate (0.33 g, 0.015 mmol) were refluxed in 250 mL of dimethoxyethane and 120 mL of water while under a nitrogen atmosphere for 21 hours. Ethyl acetate was added to the reaction mixture and the water separated. The organic layer was dried over Na$_2$SO$_4$, filtered, and the solvent removed to give the crude product which was purified on a silica gel column using 90% hexanes and 10% ethyl acetate as the eluant to obtain 10 (15.58 g) as a light brown oil.

Step 2 Bis[5-phenyl-3'-methyl(2-phenylpyridine)]iridium Dichloro Bridge Dimer (11)

13.3 g of 10 and IrCl$_3$.3H$_2$O (9.74 g) were combined and refluxed in 210 mL of 2-methoxyethanol and 100 mL and water under a nitrogen atmosphere for 21 hours. The cooled reaction mixture was filtered, and the solids were washed twice with ethanol followed by hexanes, and dried in an oven at 60° C. to yield 11 (14.05 g) as a yellow solid.

Step 3 Bis[5-phenyl-3'-methyl(2-phenylpyridine)]iridium Acetylacetonate [Ir(5-Ph-3'-Meppy)$_2$(acac)]

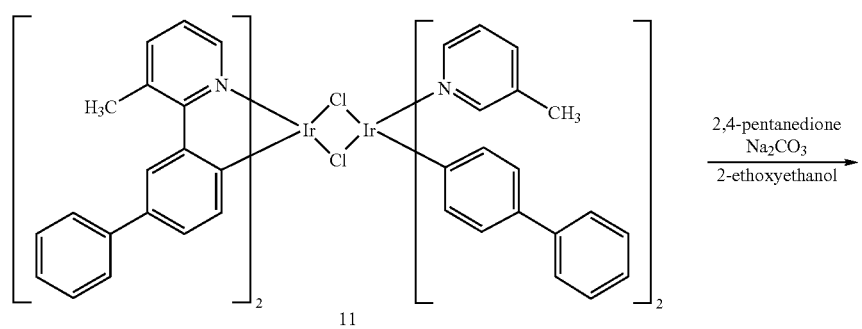

-continued

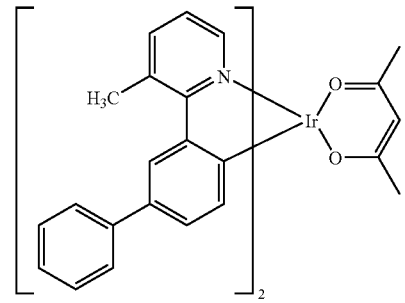

Ir(5-3'-Meppy)$_2$(acac)

11 (5.0 g), 2,4-pentanedione (3.49 g) and Na$_2$CO$_3$ (7.38 g) were combined and refluxed in 300 mL of 2-methoxyethanol under N$_2$ atmosphere for 22 hours. The cooled reaction mixture was filtered, washed three times with water, twice with ethanol, twice with hexanes and dried in an oven at 60° C. The crude product was purified using a silica gel column (70% methylene chloride/30% hexanes v/v) to obtain 2.10 g of orange solids. The material was then dissolved in a minimal amount of CH$_2$Cl$_2$ and recrystallized from methanol. The material was further purified by sublimation to yield Ir(5-Ph-3'-Meppy)$_2$(acac) (0.25 g) as the product.

EXAMPLE 4

Device Fabrication and Measurement

All devices are fabricated by high vacuum (<10$^{-7}$ Torr) thermal evaporation. The anode electrode is ~1200 Å of indium tin oxide (ITO). The cathode consists of 10 Å of LiF followed by 1,000 Å of Al. All devices are encapsulated with a glass lid sealed with an epoxy resin in a nitrogen glove box (<1 ppm of H$_2$O and O$_2$) immediately after fabrication, and a moisture getter was incorporated inside the package.

The current-voltage-luminance (IVL) characteristics and operational lifetime are measured and summarized in the table below. Typical display brightness levels of 300 cd/m$^2$ and 600 cd/m$^2$ for green and red emitting devices respectively are chosen for the comparison between different devices.

EXAMPLE 5

The organic stack consists of 100 Å thick of copper phthalocyanine (CuPc) as the hole injection layer (HIL), 400 Å of 4,4'-bis[N-(1-naphthyl)-N-phenylamino]biphenyl (α-NPD), as the hole transporting layer (HTL), 300 Å of 4,4'-bis(N-carbazolyl)biphenyl (CBP) doped with 12 wt % of Ir(5-Ph-3'-Mepq)$_2$(acac) as the emissive layer (EML). The ETL2 is 150 Å of aluminum(III)bis(2-methyl-8-quinolinato)4-phenylphenolate (BAlq). The ETL1 is 400 Å of tris(8-hydroxyquinolinato)aluminum (Alq$_3$).

EXAMPLE 6

The organic stack consists of 100 Å thick of copper phthalocyanine (CuPc) as the hole injection layer (HIL), 400 Å of 4,4'-bis[N-(1-naphthyl)-N-phenylamino]biphenyl (α-NPD), as the hole transporting layer (HTL), 300 Å of 4,4'-bis(N-carbazolyl)biphenyl (CBP) doped with 12 wt % of Ir(5-Ph-3'-Mepq)$_3$ as the emissive layer (EML). The ETL2 is 150 Å of aluminum(III)bis(2-methyl-8-quinolinato) 4-phenylphenolate (BAlq). The ETL1 is 400 Å of tris(8-hydroxyquinolinato)aluminum (Alq$_3$).

COMPARATIVE EXAMPLE 1

The organic stack consists of 100 Å thick of copper phthalocyanine (CuPc) as the hole injection layer (HIL), 400 Å of 4,4'-bis[N-(1-naphthyl)-N-phenylamino]biphenyl

| Example | Phosphorescent Material | Efficiency (cd/A) at 300 cd/m$^2$ | | % luminance retained under 40 mA/cm$^2$ current density drive | | Device CIE coordinates |
| --- | --- | --- | --- | --- | --- | --- |
| | | 300 cd/m$^2$ | 600 cd/m$^2$ | at 100 hours | at 10 hours | |
| 5 | Ir(5-Ph-3'-Mepq)$_2$(acac) | 11.8 | | 85 | | 0.66, 0.34 |
| 6 | Ir(5-Ph-3'-Mepq)$_3$ | 17 | | 86 | | 0.62, 0.38 |
| Comparative example 1 | Ir(3'-Mepq)$_2$(acac) | 13 | | 76 | | 0.65, 0.35 |
| 7 | Ir(5-Ph-3'-Meppy)$_2$(acac) | | 34 | | 82 | 0.38, 0.60 |
| Comparative example 2 | Ir(ppy)$_2$(acac) | | 19 | | 82 | 0.31, 0.64 |

(α-NPD), as the hole transporting layer (HTL), 300 Å of 4,4'-bis(N-carbazolyl)biphenyl (CBP) doped with 12 wt % of Ir(3'-Mepq)$_2$(acac) as the emissive layer (EML). The ETL2 is 150 Å of aluminum(III)bis(2-methyl-8-quinolinato) 4-phenylphenolate (BAlq). The ETL1 is 400 Å of tris(8-hydroxyquinolinato)aluminum (Alq$_3$).

EXAMPLE 7

The organic stack consists of 100 Å thick of copper phthalocyanine (CuPc) as the hole injection layer (HIL), 300 Å of 4,4'-bis[N-(1-naphthyl)-N-phenylamino]biphenyl (α-NPD), as the hole transporting layer (HTL), 300 Å of 4,4'-bis(N-carbazolyl)biphenyl (CBP) doped with 6 wt % of Ir(5-Ph-3'-Meppy)$_2$(acac) as the emissive layer (EML). The ETL2 is 100 Å of aluminum(III)bis(2-methyl-8-quinolinato) 4-phenylphenolate (BAlq). The ETL1 is 400 Å of tris(8-hydroxyquinolinato)aluminum (Alq$_3$).

COMPARATIVE EXAMPLE 2

The organic stack consists of 100 Å thick of copper phthalocyanine (CuPc) as the hole injection layer (HIL), 300 Å of 4,4'-bis[N-(1-naphthyl)-N-phenylamino]biphenyl (α-NPD), as the hole transporting layer (HTL), 300 Å of 4,4'-bis(N-carbazolyl)biphenyl (CBP) doped with 6 wt % of Ir(ppy)$_2$(acac) as the emissive layer (EML). The ETL2 is 100 Å of aluminum(III)bis(2-methyl-8-quinolinato)4-phenylphenolate (BAlq). The ETL1 is 400 Å of tris(8-hydroxyquinolinato)aluminum (Alq$_3$).

Figure 16:
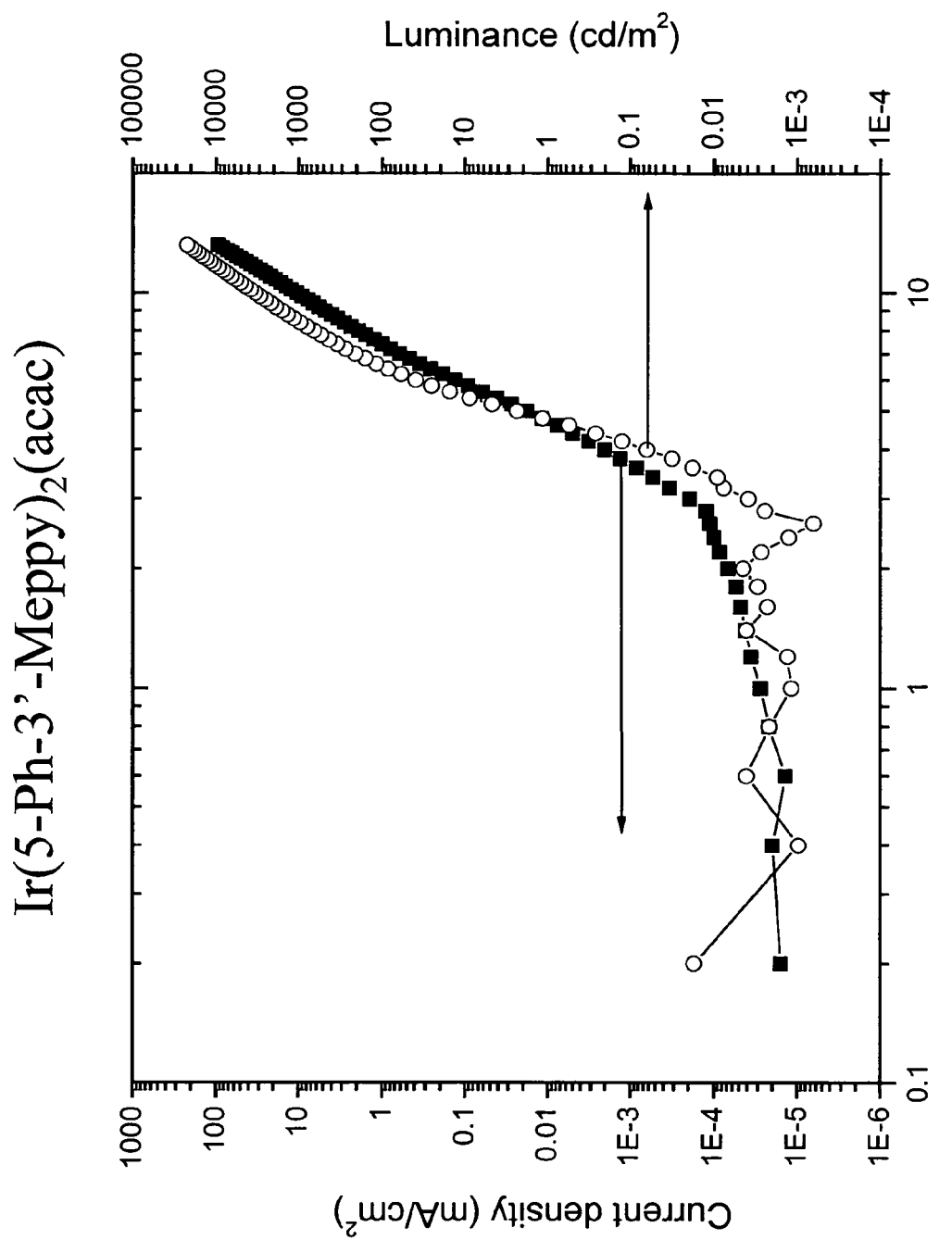
FIG. 16 shows plots of current density and brightness (cd/m$^2$) vs. voltage for a Ir(5-Ph-3'-Meppy)$_2$(acac) device at a dopant concentration of 6%.
Figure 17:
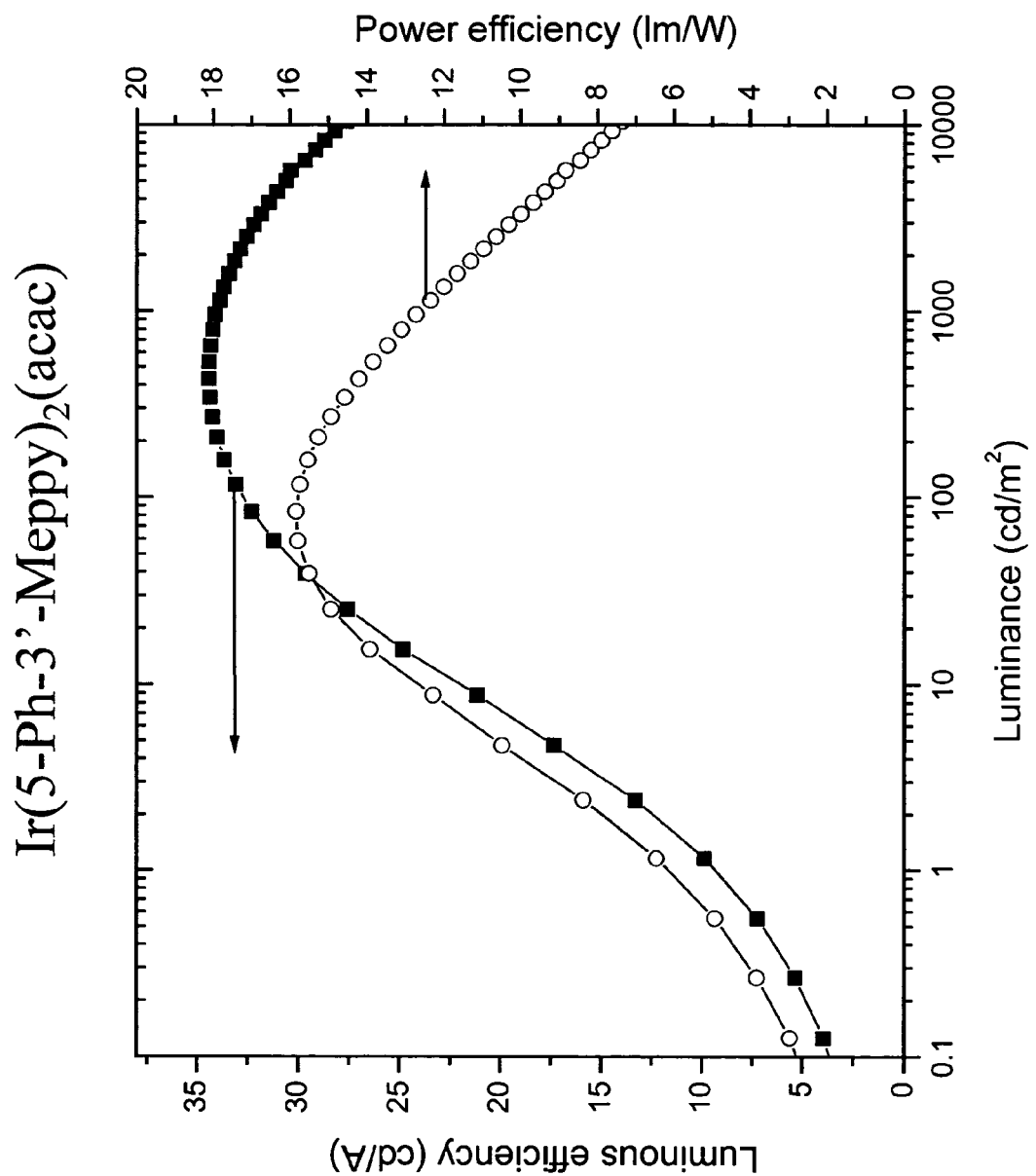
FIG. 17 shows plots of luminous efficiency (cd/A) and power efficiency (lm/W) vs. brightness (cd/m$^2$) for a Ir(5-Ph-3'-Meppy)$_2$(acac) device at a dopant concentration of 12%.
Figure 18:
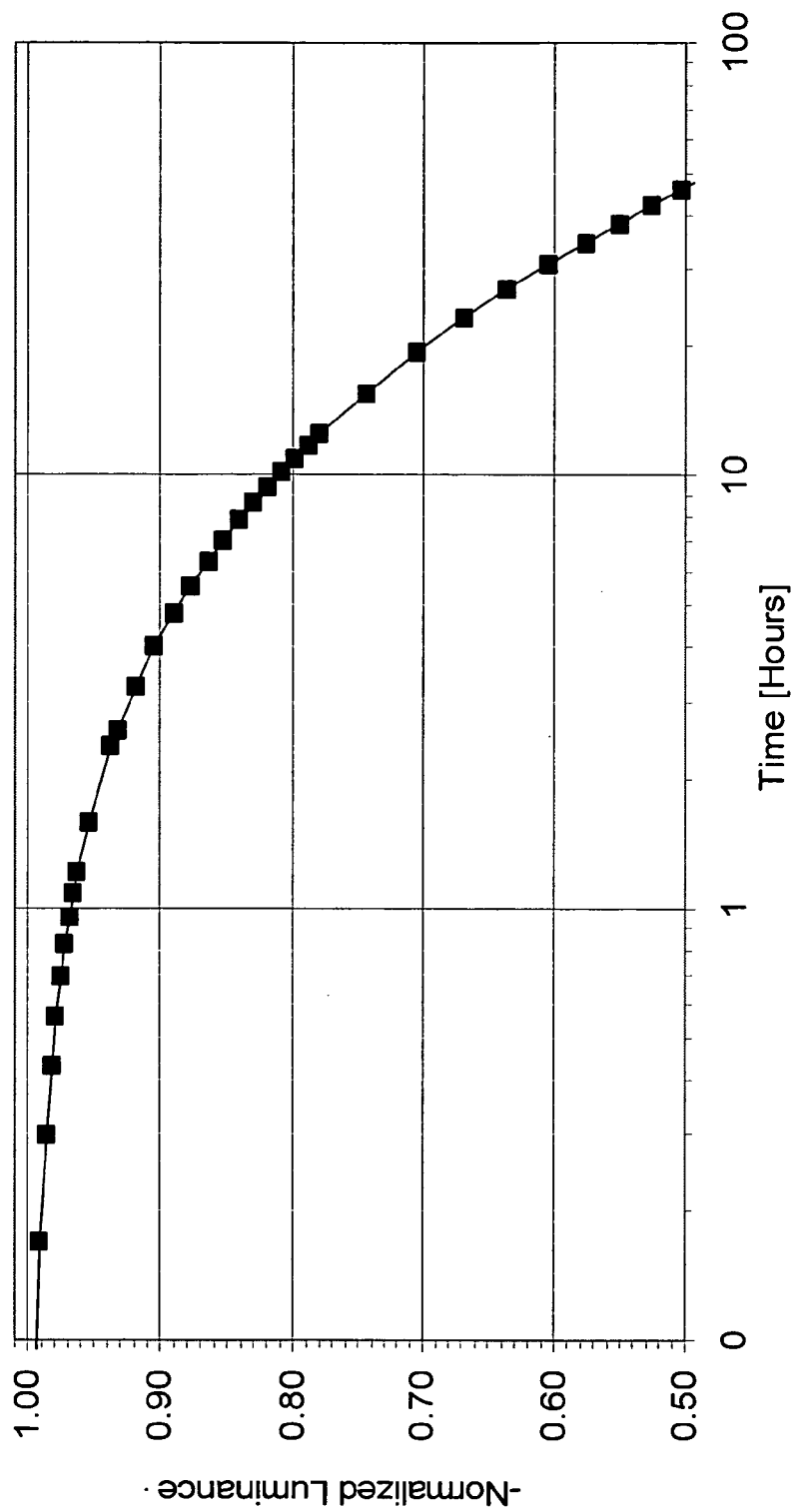
FIG. 18 shows normalized luminance decay for a Ir(5-Ph-3'-Meppy)$_2$(acac) device at a dopant concentration of 6% under constant current drive of 40 ma/cm$^2$ at room temperature.

All devices were characterized by measuring current-voltage and luminance characteristics, as well as spectral output characteristics. The device characteristics of example 5 are shown in FIGS. 3-11. The device characteristics of example 6 are shown in FIGS. 12-15. The device characteristics of example 7 are shown in FIGS. 16-18. Device stability was characterized by measuring the device luminance as a function of time under constant current drive of 40 mA/cm$^2$ at room temperature or at 60° C. with initial brightness of 480 cd/m$^2$ for example 5; 510 cd/m$^2$ for example 6; and 955 cd/m$^2$ for example 7 respectively. The summary of device performance and lifetime is given in table 1.

While the present invention is described with respect to particular examples and preferred embodiments, it is understood that the present invention is not limited to these examples and embodiments. For example, the phosphorescent materials may contain stereo and/or structural isomers. The present invention as claimed therefore includes variations from the particular examples and preferred embodiments described herein, as will be apparent to one of skill in the art.

What is claimed is:
1. A compound having the structure:

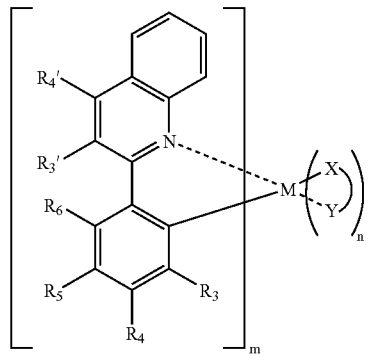

wherein
M is a metal having an atomic weight greater than 40;
R$_3$' is a substituent selected from the group consisting of alkyl, heteroalkyl, aryl, heteroaryl, and aralkyl, wherein R$_3$' is optionally substituted by one or more substituent Z;
R$_5$ is a substituent selected from the group consisting of aryl and heteroaryl, wherein aryl or heteroaryl is unsubstituted or optionally, substituted with one or more non-aromatic groups;
R$_6$' is independently H, alkyl, alkenyl, alkynyl, heteroalkyl, aryl, heteroaryl, or aralkyl;
R$_3$, R$_4$, and R$_6$ are each independently selected from the group consisting of H, alkyl, alkenyl, alkynyl, alkylaryl, CN, perfluoroalkyl, trifluorovinyl, CO$_2$R, C(O)R, NR$_2$, NO$_2$, OR, halo, aryl, heteroaryl, substituted aryl, substituted heteroaryl or a heterocyclic group;

wherein
M is a metal having an atomic weight greater than 40;
R$_3$' is a substituent selected from the group consisting of alkyl, heteroallcyl, aryl, heteroaryl, and aralkyl, wherein R$_3$' is optionally substituted by one or more substituent Z;
R$_5$ is a substituent selected from the group consisting of aryl and heteroaryl, wherein aryl or heteroaryl is unsubstituted or optionally, substituted with one or more non-aromatic groups;
R$_4$' is independently H, alkyl, alkenyl, alkynyl, heteroalkyl, aryl, heteroaryl, or aralkyl;
R$_3$, R$_4$, and R$_6$ are each independently selected from the group consisting of H, alkyl, alkenyl, alkynyl, alkylaryl, CN, perfluoroalkyl, trifluorovinyl, CO$_2$R, C(O)R, NR$_2$, NO$_2$, OR, halo, aryl, heteroaryl, substituted aryl, substituted heteroaryl or a heterocyclic group;
each R is independently H, alkyl, alkenyl, alkynyl, heteroalkyl, aryl, heteroaryl, or aralkyl; wherein R is optionally substituted by one or more substituent Z;
each Z is independently a halogen, R', O—R', N(R')$_2$, SR', C(O)R', C(O)OR', C(O)N(R')$_2$, CN, NO$_2$, SO$_2$, SOR', SO$_2$R', or SO$_3$R';
each R' is independently H, alkyl, perhaloalkyl, alkenyl, alkynyl, heteroalkyl, aralkyl, aryl, or heteroaryl;
(X—Y) is an ancillary ligand;
m is a value from 1 to the maximum number of ligands that may be attached to the metal; and m+n is the maximum number of ligands that may be attached to the metal.

2. A compound having the structure:

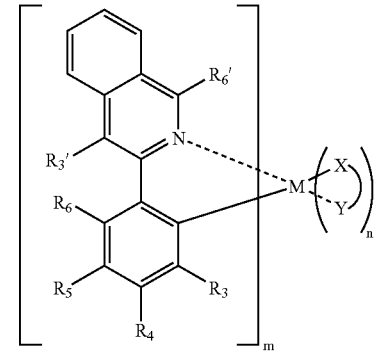

each R is independently H, alkyl, alkenyl, alkynyl, heteroalkyl, aryl, heteroaryl, or aralkyl; wherein R is optionally substituted by one or more substituent Z;

each Z is independently a halogen, R', O—R', N(R')$_2$, SR', C(O)R', C(O)R', C(O)N(R')$_2$, CN, NO$_2$, SO$_2$, SOR', SO$_2$R', or SO$_3$R';

each R' is independently H, alkyl, perhaloalkyl, alkenyl, alkynyl, heteroalkyl, aralkyl, aryl, or heteroaryl;

(X—Y) is an ancillary ligand;

m is a value from 1 to the maximum number of ligands that may be attached to the metal; and m+n is the maximum number of ligands that may be attached to the metal.

3. A compound having the structure:

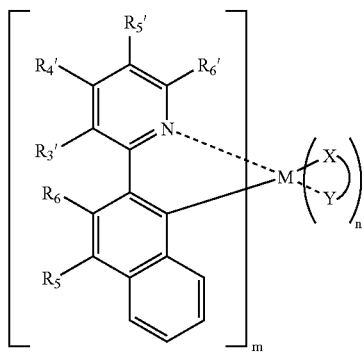

wherein

M is a metal having an atomic weight greater than 40;

$R_3'$ is a substituent selected from the group consisting of alkyl, heteroalkyl, aryl, heteroaryl, and aralkyl, wherein $R_3'$ is optionally substituted by one or more substituent Z;

$R_5$ is a substituent selected from the group consisting of aryl and heteroaryl, wherein aryl or heteroaryl is unsubstituted or optionally, substituted with one or more non-aromatic groups;

$R_4'$, $R_5'$, and $R_6'$ are each independently H, alkyl, alkenyl, alkynyl, heteroalkyl, aryl, heteroaryl, or aralkyl; $R_6$ is independently selected from the group consisting of H, alkyl, alkenyl, alkynyl, alkylaryl, CN, perfluoroalkyl, trifluorovinyl, CO$_2$R, C(O)R, NR$_2$, NO$_2$, OR, halo, aryl, heteroaryl, substituted aryl, substituted heteroaryl or a heterocyclic group;

each R is independently H, alkyl, alkenyl, alkynyl, heteroalkyl, aryl, heteroaryl, or aralkyl; wherein R is optionally substituted by one or more substituent Z;

each Z is independently a halogen, R', O—R', N(R')$_2$, SR', C(O)R', C(O)OR', C(O)N(R')$_2$, CN, NO$_2$, SO$_2$, SOR', SO$_2$R', or SO$_3$R';

each R' is independently H, alkyl, perhaloalkyl, alkenyl, alkynyl, heteroalkyl, aralkyl, aryl, or heteroaryl;

(X—Y) is an ancillary ligand;

m is a value from 1 to the maximum number of ligands that may be attached to the metal; and m+n is the maximum number of ligands that may be attached to the metal.

4. A compound having the structure:

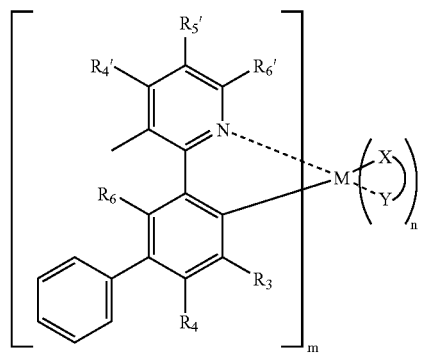

wherein

M is a metal having an atomic weight greater than 40;

$R_4'$ is independently H, alkyl, alkenyl, alkynyl, heteroalkyl, aryl, heteroaryl, or aralkyl;

$R_3$, $R_4$, and $R_6$ are each independently selected from the group consisting of H, alkyl, alkenyl, alkynyl, alkylaryl, CN, perfluoroalkyl, trifluorovinyl, CO$_2$R, C(O)R, NR$_2$, NO$_2$, OR, halo, aryl, heteroaryl, substituted aryl, substituted heteroaryl or a heterocyclic group;

each R is independently H, alkyl, alkenyl, alkynyl, heteroalkyl, aryl, heteroaryl, or aralkyl; wherein R is optionally substituted by one or more substituent Z;

each Z is independently a halogen, R', O—R', N(R')$_2$, SR', C(O)R', C(O)OR', C(O)N(R')$_2$, CN, NO$_2$, SO$_2$, SOR', SO$_2$R', or SO$_3$R';

each R' is independently H, alkyl, perhaloalkyl, alkenyl, alkynyl, heteroalkyl, aralkyl, aryl, or heteroaryl;

(X—Y) is an ancillary ligand;

m is a value from 1 to the maximum number of ligands that may be attached to the metal; and m+n is the maximum number of ligands that may be attached to the metal; and $R_5'$ and $R_6'$ are H, and additionally or alternatively, together form a fused 4- to 7-member cyclic group, wherein said cyclic group is cycloalkyl, cycloheteroalkyl, aryl, or heteroaryl.

5. The compound of claim 4, wherein M is selected from the group consisting of Ir, Pt, Pd, Rh, Re, Ru, Os, Tl, Pb, Bi, In, Sn, Sb, Te, Au, and Ag.

6. The compound of claim 5, wherein M is Ir.

7. The compound of claim 6, having the structure:

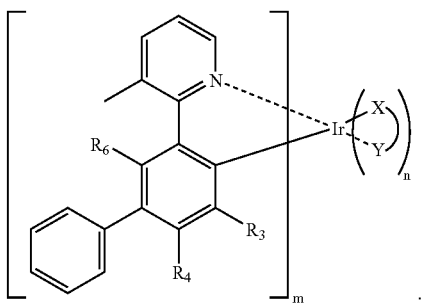

8. The compound of claim 7, having the structure:

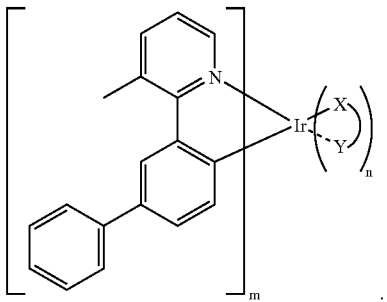

9. The compound of claim 8, wherein m is 3 and n is zero, such that the compound has the structure:

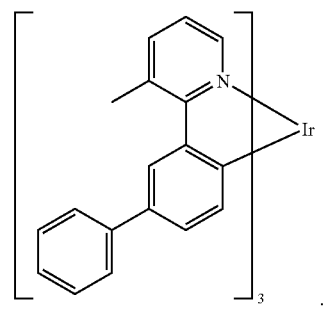

10. The compound of claim 8, wherein m is 2 and n is 1.

11. The compound of claim 10, having the structure:

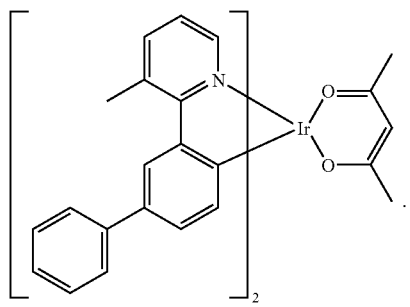

12. The compound of claim 6, having the structure:

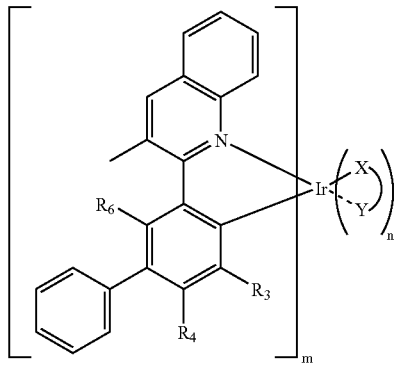

13. The compound of claim 12, having the structure:

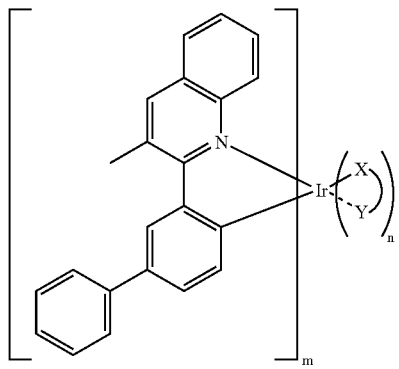

14. The compound of claim 13, wherein m is 3 and n is zero, such that the compound has the structure:

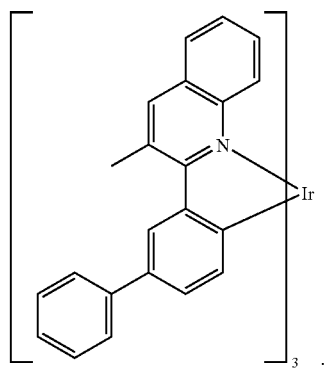

15. The compound of claim 13, wherein m is 2 and n is 1.

16. The compound of claim 15, having the structure:

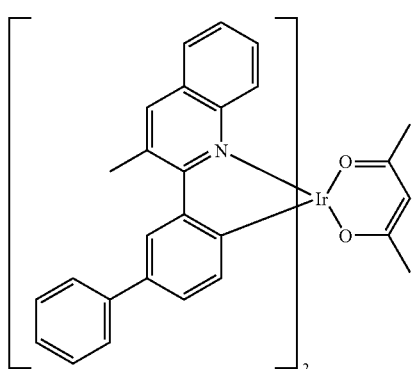

17. A compound of comprising a ligand having the structure:

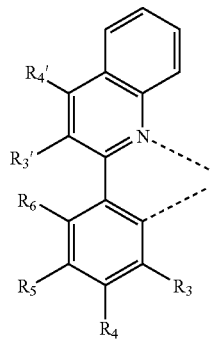

wherein
- R₃' is a substituent selected from the group consisting of alkyl, heteroalkyl, aryl, heteroaryl, and aralkyl, wherein R₃' is optionally substituted by one or more substituent Z;
- R₅ is a substituent selected from the group consisting of aryl and heteroaryl, wherein aryl or heteroaryl is unsubstituted or optionally, substituted with one or more non-aromatic groups;
- the nitrogen atom N is coordinated to a metal having an atomic weight greater than 40;
- R₄' is independently H, alkyl, alkenyl, alkynyl, heteroalkyl, aryl, heteroaryl, aralkyl;
- R₃, R₄, and R₆ are each independently selected from the group consisting of H, alkyl, alkenyl, alkynyl, alkylaryl, CN, perfluoroalkyl, trifluorovinyl, CO₂R, C(O)R, NR₂, NO₂, OR, halo, aryl, heteroaryl, substituted aryl, substituted heteroaryl or a heterocyclic group;
- each R is independently H, alkyl, alkenyl, alkynyl, heteroalkyl, aryl, heteroaryl, or aralkyl; wherein R is optionally substituted by one or more substituent Z;
- each Z is independently a halogen, R', O—R', N(R')₂, SR', C(O)R', C(O)OR', C(O)N(R')₂, CN, NO₂, SO₂, SOR', SO₂R', or SO₃R';
  - each R' is independently H, alkyl, perhaloalkyl, alkenyl, alkynyl, heteroalkyl, aralkyl, aryl, or heteroaryl.

18. A compound comprising a ligand having the structure:

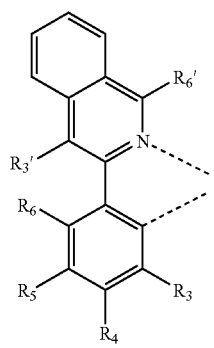

wherein
- R₃' is a substituent selected from the group consisting of alkyl, heteroalkyl, aryl, heteroaryl, and aralkyl, wherein R₃' is optionally substituted by one or more substituent Z;
- R₅ is a substituent selected from the group consisting of aryl and heteroaryl, wherein aryl or heteroaryl is unsubstituted or optionally, substituted with one or more non-aromatic groups;
- the nitrogen atom N is coordinated to a metal having an atomic weight greater than 40;
- R₆' is independently H, alkyl, alkenyl, alkynyl, heteroalkyl, aryl, heteroaryl, or aralkyl;
- R₃, R₄, and R₆ are each independently selected from the group consisting of H, alkyl, alkenyl, alkynyl, alkylaryl, CN, perfluoroalkyl, trifluorovinyl, CO₂R, C(O)R, NR₂, NO₂, OR, halo, aryl, heteroaryl, substituted aryl, substituted heteroaryl or a heterocyclic group;
- each R is independently H, alkyl, alkenyl, alkynyl, heteroalkyl, aryl, heteroaryl, or aralkyl; wherein R is optionally substituted by one or more substituent Z;
- each Z is independently a halogen, R', O—R', N(R')₂, SR', C(O)R', C(O)OR', C(O)N(R')₂, CN, NO₂, SOR', SO₂R', or SO₃R';
- each R' is independently H, alkyl, perhaloalkyl, alkenyl, alkynyl, heteroalkyl, aralkyl, aryl, or heteroaryl.

19. A compound comprising a ligand having the structure:

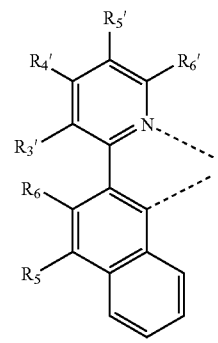

wherein R₃' is a substituent selected from the group consisting of alkyl, heteroalkyl, aryl, heteroaryl, and aralkyl, wherein R₃' is optionally substituted by one or more substituent Z;
- R₅ is a substituent selected from the group consisting of aryl and heteroaryl, wherein aryl or heteroaryl is unsubstituted or optionally, substituted with one or more non-aromatic groups;
- the nitrogen atom N is coordinated to a metal having an atomic weight greater than 40;
- R₄, R₅, and R₆' are each independently H, alkyl, alkenyl, alkynyl, heteroalkyl, aryl, heteroaryl, or aralkyl;
- R₆ is independently selected from the group consisting of H, alkyl, alkenyl, alkynyl, alkylaryl, CN, perfluoroalkyl, trifluorovinyl, CO₂R, C(O)R, NR₂, NO₂, OR, halo, aryl, heteroaryl, substituted aryl, substituted heteroaryl or a heterocyclic group;
- each R is independently H, alkyl, alkenyl, alkynyl, heteroalkyl, aryl, heteroaryl, or aralkyl; wherein R is optionally substituted by one or more substituent Z;
- each Z is independently a halogen, R', O—R', N(R')₂, SR', C(O)R', C(O)OR', C(O)N(R')₂, CN, NO₂, SO₂, SOR', SO₂R', or SO₃R';
- each R' is independently H, alkyl, perhaloalkyl, alkenyl, alkynyl, heteroalkyl, aralkyl, aryl, or heteroaryl.

20. A compound comprising a ligand having the structure:

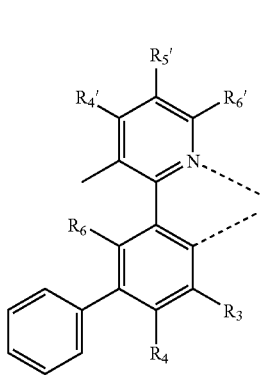

wherein the nitrogen atom N is coordinated to a metal having an atomic weight greater than 40;

$R_4'$ is independently H, alkyl, alkenyl, alkynyl, heteroalkyl, aryl, heteroaryl, or aralkyl;

$R_3$, $R_4$, and $R_6$ are each independently selected from the group consisting of H, alkyl, alkenyl, alkynyl, alkylaryl, CN, perfluoroalkyl, trifluorovinyl, $CO_2R$, $C(O)R$, $NR_2$, $NO_2$, OR, halo, aryl, heteroaryl, substituted aryl, substituted heteroaryl or a heterocyclic group;

each R is independently H, alkyl, alkenyl, alkynyl, heteroalkyl, aryl, heteroaryl, or aralkyl; wherein R is optionally substituted by one or more substituent Z;

each Z is independently a halogen, R', O—R', $N(R')_2$, SR', $C(O)R'$, $C(O)OR'$, $C(O)N(R')_2$, CN, $NO_2$, $SO_2$, SOR', $SO_2R'$, or $SO_3R'$;

each R' is independently H, alkyl, perhaloalkyl, alkenyl, alkynyl, heteroalkyl, aralkyl, aryl, or heteroaryl; and $R_5'$ and $R_6'$ are H, and additionally or alternatively, together form a fused 4- to 7-member cyclic group, wherein said cyclic group is cycloalkyl, cycloheteroalkyl, aryl, or heteroaryl.

21. The compound of claim 20, wherein the ligand has the structure:

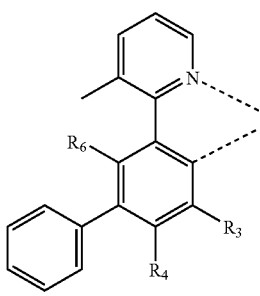

22. The compound of claim 21, wherein the ligand has the structure:

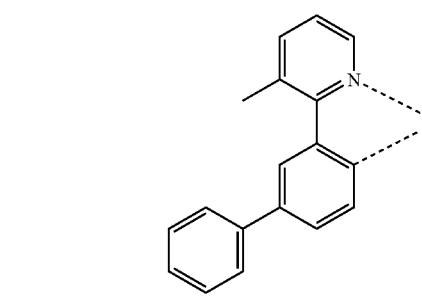

23. The compound of claim 20, wherein the ligand has the structure:

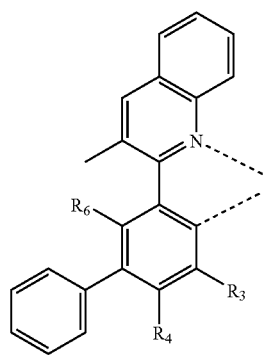

24. The compound of claim 23, wherein the ligand has the structure:

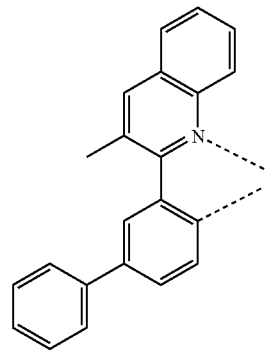

25. An organic light emitting device, comprising:
(a) an anode;
(b) a cathode; and
(c) an emissive layer disposed between the anode and the cathode, wherein the emissive layer comprises an emissive material having the structure:

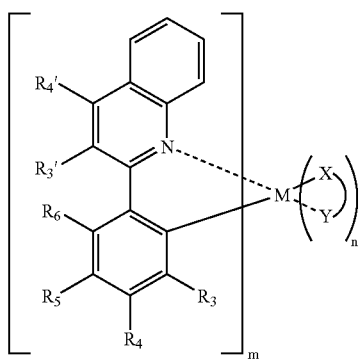

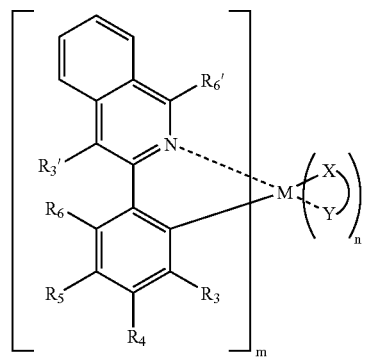

wherein

M is a metal having an atomic weight greater than 40;

$R_3'$ is a substituent selected from the group consisting of alkyl, heteroalkyl, aryl, heteroaryl, and aralkyl, wherein $R_3'$ is optionally substituted by one or more substituent Z;

$R_5$ is a substituent selected from the group consisting of aryl and heteroaryl, wherein aryl or heteroaryl is unsubstituted or optionally, substituted with one or more non-aromatic groups;

$R_4'$ is independently H, alkyl, alkenyl, alkynyl, heteroalkyl, aryl, heteroaryl, or aralkyl;

$R_3$, $R_4$, and $R_6$ are each independently selected from the group consisting of H, alkyl, alkenyl, alkynyl, alkylaryl, CN, perfluoroalkyl, trifluorovinyl, $CO_2R$, C(O)R, $NR_2$, $NO_2$, OR, halo, aryl, heteroaryl, substituted aryl, substituted heteroaryl or a heterocyclic group;

each R is independently H, alkyl, alkenyl, alkynyl, heteroalkyl, aryl, heteroaryl, or aralkyl; wherein R is optionally substituted by one or more substituents Z;

each Z is independently a halogen R', O—R', $N(R')_2$, SR', C(O)R', C(O)OR', $C(O)N(R')_2$, CN, $NO_2$, $SO_2$, SOR', $SO_2R'$, or $SO_3R'$;

each R' is independently H, alkyl, perhaloalkyl, alkenyl, alkynyl, heteroalkyl, aralkyl, aryl, or heteroaryl;

(X—Y) is an ancillary ligand;

m is a value from 1 to the maximum number of ligands that may be attached to the metal; and m+n is the maximum number of ligands that may be attached to the metal.

26. An organic light emitting device, comprising:

(a) an anode;

(b) a cathode; and (c) an emissive layer disposed between the anode and the cathode, wherein the emissive layer comprises an emissive material having the structure:

wherein

M is a metal having an atomic weight greater than 40;

$R_3'$ is a substituent selected from the group consisting of alkyl, heteroalkyl, aryl, heteroaryl, and aralkyl, wherein $R_3'$ is optionally substituted by one or more substituent Z;

$R_5$ is a substituent selected from the group consisting of aryl and heteroaryl, wherein aryl or heteroaryl is unsubstituted or optionally, substituted with one or more non-aromatic groups;

$R_6'$ is independently H, alkyl, alkenyl, alkynyl, heteroalkyl, aryl, heteroaryl, or aralkyl;

$R_3$, $R_4$, and $R_6$ are each independently selected from the group consisting of H, alkyl, alkenyl, alkynyl, alkylaryl, CN, perfluoroalkyl, trifluorovinyl, $CO_2R$, C(O)R, $NR_2$, $NO_2$, OR, halo, aryl, heteroaryl, substituted aryl, substituted heteroaryl or a heterocyclic group;

each R is independently H, alkyl, alkenyl, alkynyl, heteroalkyl, aryl, heteroaryl, or aralkyl; wherein R is optionally substituted by one or more substituents Z;

each Z is independently a halogen, R', O—R', $N(R')_2$, SR', C(O)R', C(O)OR', $C(O)N(R')_2$, CN, $NO_2$, $SO_2$, SOR', $SO_2R'$, or $SO_3R'$;

each R' is independently H, alkyl, perhaloalkyl, alkenyl, alkynyl, heteroalkyl, aralkyl, aryl, or heteroaryl;

(X—Y) is an ancillary ligand;

m is a value from 1 to the maximum number of ligands that may be attached to the metal; and m+n is the maximum number of ligands that may be attached to the metal.

27. An organic light emitting device, comprising:

(a) an anode;

(b) a cathode; and (c) an emissive layer disposed between the anode and the cathode, wherein the emissive layer comprises an emissive material having the structure:

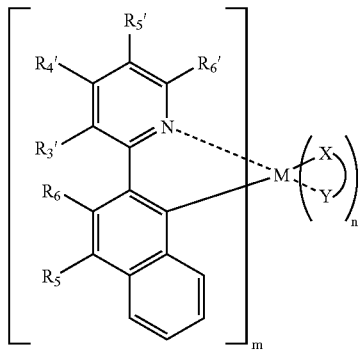

wherein

M is a metal having an atomic weight greater than 40;

$R_3'$ is a substituent selected from the group consisting of alkyl, heteroalkyl, aryl, heteroaryl, and aralkyl, wherein $R_3'$ is optionally substituted by one or more substituent Z;

$R_5$ is a substituent selected from the group consisting of aryl and heteroaryl, wherein aryl or heteroaryl is unsubstituted or optionally, substituted with one or more non-aromatic groups;

$R_4'$, $R_5'$, and $R_6'$ are each independently H, alkyl, alkenyl, alkynyl, heteroalkyl, aryl, heteroaryl, or aralkyl; $R_6$ is independently selected from the group consisting of H, alkyl, alkenyl, alkynyl, alkylaryl, CN, perfluoroalkyl, trifluorovinyl, $CO_2R$, $C(O)R$, $NR_2$, $NO_2$, OR, halo, aryl, heteroaryl, substituted aryl, substituted heteroaryl or a heterocyclic group;

each R is independently H, alkyl, alkenyl, alkynyl, heteroalkyl, aryl, heteroaryl, or aralkyl; wherein R is optionally substituted by one or more substituents Z;

each Z is independently a halogen, R', O—R', $N(R')_2$, SR', $C(O)R'$, $C(O)OR'$, $C(O)N(R')_2$, CN, $NO_2$, $SO_2$, SOR', $SO_2R'$, or $SO_3R'$;

each R' is independently H, alkyl, perhaloalkyl, alkenyl, alkynyl, heteroalkyl, aralkyl, aryl, or heteroaryl;

(X—Y) is an ancillary ligand;

m is a value from 1 to the maximum number of ligands that may be attached to the metal; and m+n is the maximum number of ligands that may be attached to the metal.

28. An organic light emitting device, comprising:

(a) an anode;

(b) a cathode; and (c) an emissive layer disposed between the anode and the cathode, wherein the emissive layer comprises an emissive material having the structure:

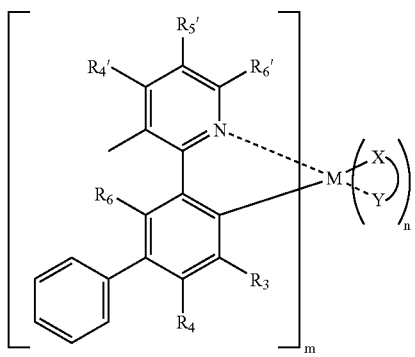

wherein

M is a metal having an atomic weight greater than 40;

$R_4'$ is independently H, alkyl, alkenyl, alkynyl, heteroalkyl, aryl, heteroaryl, or aralkyl;

$R_3$, $R_4$, and $R_6$ are each independently selected from the group consisting of H, alkyl, alkenyl, alkynyl, alkylaryl, CN, perfluoroalkyl, trifluorovinyl, $CO_2R$, $C(O)R$, $NR_2$, $NO_2$, OR, halo, aryl, heteroaryl, substituted aryl, substituted heteroaryl or a heterocyclic group;

each R is independently H, alkyl, alkenyl, alkynyl, heteroalkyl, aryl, heteroaryl, or aralkyl; wherein R is optionally substituted by one or more substituent Z;

each Z is independently a halogen, R', O—R', $N(R')_2$, SR', $C(O)R'$, $C(O)OR'$, $C(O)N(R')_2$, CN, $NO_2$, $SO_2$, SOR', $SO_2R'$, or $SO_3R'$;

each R' is independently H, alkyl, perhaloalkyl, alkenyl, alkynyl, heteroalkyl, aralkyl, aryl, or heteroaryl;

(X—Y) is an ancillary ligand;

m is a value from 1 to the maximum number of ligands that may be attached to the metal; and m+n is the maximum number of ligands that may be attached to the metal; and $R_5'$ and $R_6'$ are H, and additionally or alternatively, together form a fused 4- to 7-member cyclic group, wherein said cyclic group is cycloalkyl, cycloheteroalkyl, aryl, or heteroaryl.

29. The device of claim 28, wherein M is selected from the group consisting of Ir, Pt, Pd, Rh, Re, Ru, Os, Tl, Pb, Bi, In, Sn, Sb, Te, Au, and Ag.

30. The device of claim 29, wherein M is Ir.

31. The device of claim 30, wherein the compound has the structure:

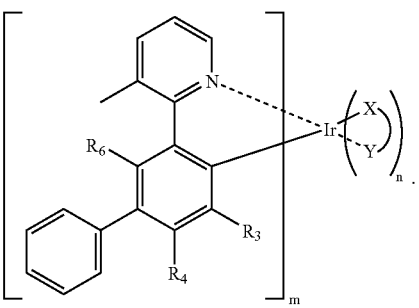

32. The device of claim 31, wherein the compound has the structure:

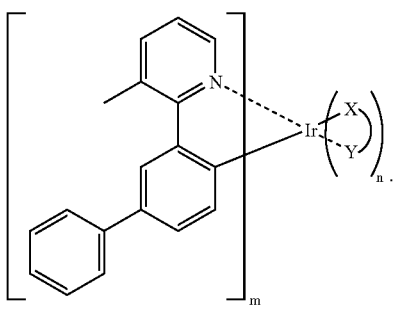

33. The device of claim 32, wherein m is 3 and n is zero, such that the compound has the structure:

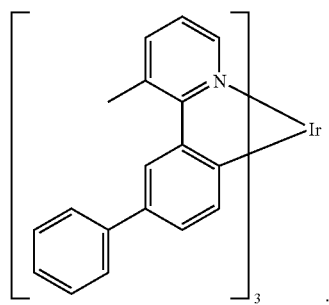

34. The device of claim 32, wherein m is 2 and n is 1.

35. The device of claim 34, wherein the compound has the structure:

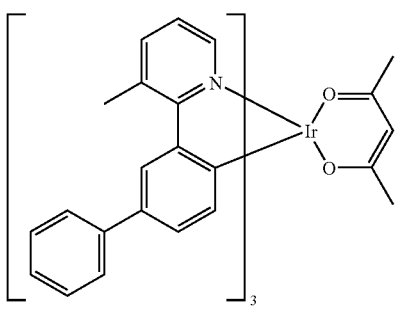

36. The device of claim 30, wherein the compound has the structure:

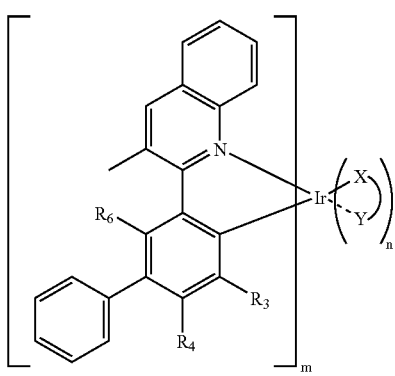

37. The device of claim 36, wherein the compound has the structure:

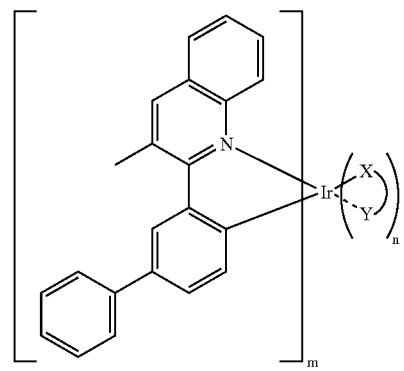

38. The device of claim 37, wherein m is 3 and n is zero, such that the compound has the structure:

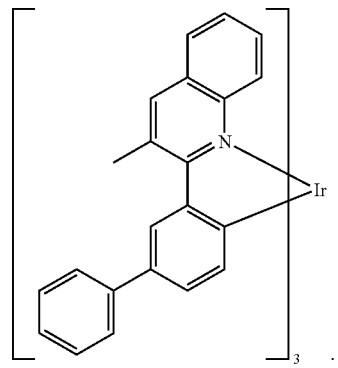

39. The device of claim 37, wherein m is 2 and n is 1.

40. The device of claim 39, wherein the compound has the structure:

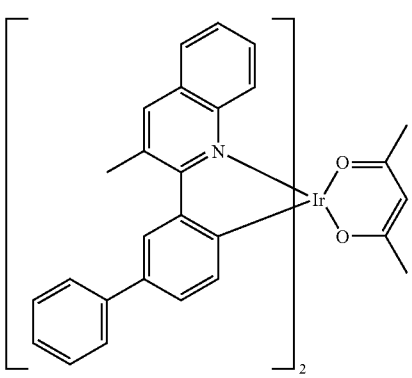

41. The device of claim 28, wherein the device is incorporated into a consumer product.

42. An organic light emitting device, comprising:
(a) an anode;
(b) a cathode; and
(c) an emissive layer disposed between the anode and the cathode, wherein the emissive layer comprises an emissive material having a ligand with the structure:

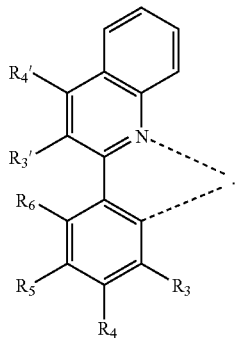

wherein
- $R_3'$ is a substituent selected from the group consisting of alkyl, heteroalkyl, aryl, heteroaryl, and aralkyl, wherein $R_3'$ is optionally substituted by one or more substituent Z;
- $R_5$ is a substituent selected from the group consisting of aryl and heteroaryl, wherein aryl or heteroaryl is unsubstituted or optionally, substituted with one or more non-aromatic groups;
- the nitrogen atom N is coordinated to a metal having an atomic weight greater than 40;
- $R_4$ is independently H, alkyl, alkenyl, alkynyl, heteroalkyl, aryl, heteroaryl, aralkyl;
- $R_3$, $R_4$, and $R_6$ are each independently selected from the group consisting of H, alkyl, alkenyl, alkynyl, alkylaryl, CN, perfluoroalkyl, trifluorovinyl, $CO_2R$, $C(O)R$, $NR_2$, $NO_2$, OR, halo, aryl, heteroaryl, substituted aryl, substituted heteroaryl or a heterocyclic group;
- each R is independently H, alkyl, alkenyl, alkynyl, heteroalkyl, aryl, heteroaryl, or aralkyl; wherein R is optionally substituted by one or more substituent Z;
- each Z is independently a halogen, R', O—R', $N(R')_2$, SR', C(O)R', C(O)OR', C(O')N(R')_2, CN, $NO_2$, $SO_2$, SOR', $SO_2R'$, or $SO_3R'$;
  - each R' is independently H, alkyl, perhaloalkyl, alkenyl, alkynyl, heteroalkyl, aralkyl, aryl, or heteroaryl.

43. An organic light emitting device, comprising:
(a) an anode;
(b) a cathode; and
(c) an emissive layer disposed between the anode and the cathode, wherein the emissive layer comprises an emissive material having a ligand with the structure:

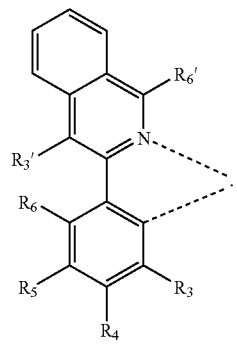

wherein
- $R_3'$ is a substituent selected from the group consisting of alkyl, heteroalkyl, aryl, heteroaryl, and aralkyl, wherein $R_3'$ is optionally substituted by one or more substituent Z;
- $R_5$ is a substituent selected from the group consisting of aryl and heteroaryl, wherein aryl or heteroaryl is unsubstituted or optionally, substituted with one or more non-aromatic groups;
- the nitrogen atom N is coordinated to a metal having an atomic weight greater than 40;
- $R_6'$ is independently H, alkyl, alkenyl, alkynyl, heteroalkyl, aryl, heteroaryl, aralkyl; $R_3$, $R_4$, and $R_6$ are each independently selected from the group consisting of H, alkyl, alkenyl, alkynyl, alkylaryl, CN, perfluoroalkyl, trifluorovinyl, $CO_2R$, $C(O)R$, $NR_2$, $NO_2$, OR, halo, aryl, heteroaryl, substituted aryl, substituted heteroaryl or a heterocyclic group;
- each R is independently H, alkyl, alkenyl, alkynyl, heteroalkyl, aryl, heteroaryl, or aralkyl; wherein R is optionally substituted by one or more substituent Z;
- each Z is independently a halogen, R', O—R', $N(R')_2$, SR', C(O)R', C(O)OR', $C(O)N(R')_2$, CN, $NO_2$, $SO_2$, SOR', $SO_2R'$, or $SO_3R'$;
- each R' is independently H, alkyl, perhaloalkyl, alkenyl, alkynyl, heteroalkyl, aralkyl, aryl, or heteroaryl.

44. An organic light emitting device, comprising:
(a) an anode;
(b) a cathode; and
(c) an emissive layer disposed between the anode and the cathode, wherein the emissive layer comprises an emissive material having a ligand with the structure:

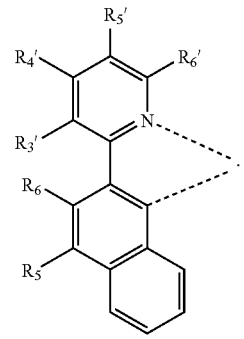

wherein
- $R_3'$ is a substituent selected from the group consisting of alkyl, heteroalkyl, aryl, heteroaryl, and aralkyl, wherein $R_3'$ is optionally substituted by one or more substituent Z;
- $R_5$ is a substituent selected from the group consisting of aryl and heteroaryl, wherein aryl or heteroaryl is unsubstituted or optionally, substituted with one or more non-aromatic groups;
- the nitrogen atom N is coordinated to a metal having an atomic weight greater than 40;
- $R_4'$, $R_5'$, and $R_6'$ are each independently H, alkyl, alkenyl, alkynyl, heteroalkyl, aryl, heteroaryl, aralkyl;
- $R_6$ is independently selected from the group consisting of H, alkyl, alkenyl, alkynyl, alkylaryl, CN, perfluoroalkyl, trifluorovinyl, $CO_2R$, $C(O)R$, $NR_2$, $NO_2$, OR, halo, aryl, heteroaryl, substituted aryl, substituted heteroaryl or a heterocyclic group;
- each R is independently H, alkyl, alkenyl, alkynyl, heteroalkyl, aryl, heteroaryl, or aralkyl; wherein R is optionally substituted by one or more substituent Z;

each Z is independently a halogen, R', O—R', N(R')$_2$, SR', C(O)R', C(O)OR', C(O)N(R')$_2$, CN, NO$_2$, SO$_2$, SOR', SO$_2$R', or SO$_3$R';

each R' is independently H, alkyl, perhaloalkyl, alkenyl, alkynyl, heteroalkyl, aralkyl, aryl, or heteroaryl.

45. An organic light emitting device, comprising:
(a) an anode;
(b) a cathode; and
(c) an emissive layer disposed between the anode and the cathode, wherein the emissive layer comprises an emissive material having a ligand with the structure:

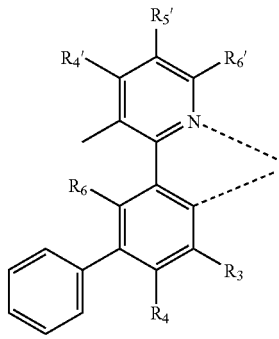

wherein
the nitrogen atom N is coordinated to a metal having an atomic weight greater than 40;
$R_4'$ is independently H, alkyl, alkenyl, alkynyl, heteroalkyl, aryl, heteroaryl, aralkyl;
$R_3$, $R_4$, and $R_6$ are each independently selected from the group consisting of H, alkyl, alkenyl, alkynyl, alkylaryl, CN, perfluoroalkyl, trifluorovinyl, CO$_2$R, C(O)R, NR$_2$, NO$_2$, OR, halo, aryl, heteroaryl, substituted aryl, substituted heteroaryl or a heterocyclic group;
each R is independently H, alkyl, alkenyl, alkynyl, heteroalkyl, aryl, heteroaryl, or aralkyl; wherein R is optionally substituted by one or more substituent Z;
each Z is independently a halogen, R', O—R', N(R')$_2$, SR', C(O)R', C(O)OR', C(O)N(R')$_2$, CN, NO$_2$, SO$_2$, SOR', SO$_2$R', or SO$_3$R';
each R' is independently H, alkyl, perhaloalkyl, alkenyl, alkynyl, heteroalkyl, aralkyl, aryl, or heteroaryl; and
$R_5'$ and $R_6'$ are H, and additionally or alternatively, together form a fused 4- to 7-member cyclic group, wherein said cyclic group is cycloalkyl, cycloheteroalkyl, aryl, or heteroaryl.

46. The device of claim 45, wherein the ligand has the structure:

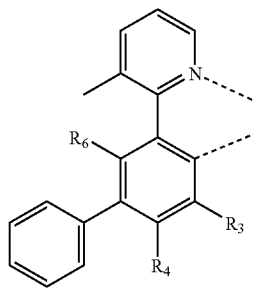

47. The device of claim 46, wherein the ligand has the structure:

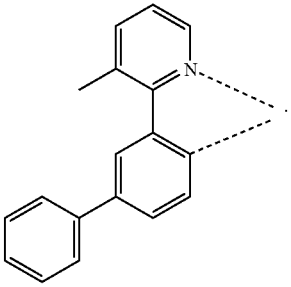

48. The device of claim 45, wherein the ligand has the structure:

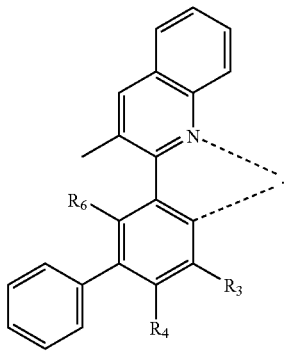

49. The device of claim 48, wherein the ligand has the structure:

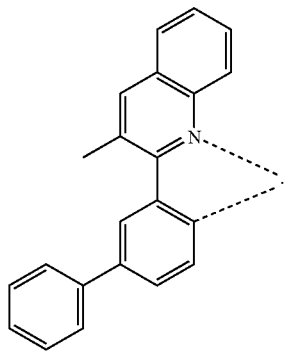

50. The device of claim 45, wherein the device is incorporated into a consumer product.

* * * * *